US007608755B2

(12) United States Patent
Shi et al.

(10) Patent No.: US 7,608,755 B2
(45) Date of Patent: Oct. 27, 2009

(54) INOSITOL POLYPHOSPHATE KINASE GENES AND USES THEREOF

(75) Inventors: Jinrui Shi, Johnston, IA (US); Hongyu Wang, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 428 days.

(21) Appl. No.: 11/439,595

(22) Filed: May 24, 2006

(65) Prior Publication Data

US 2006/0272046 A1 Nov. 30, 2006

Related U.S. Application Data

(63) Continuation-in-part of application No. 10/042,894, filed on Jan. 9, 2002, now Pat. No. 7,067,720.

(60) Provisional application No. 60/261,465, filed on Jan. 12, 2001.

(51) Int. Cl.
*C12N 15/82* (2006.01)
*C12N 15/63* (2006.01)
*C12N 15/11* (2006.01)
*A01H 5/00* (2006.01)
*A01H 5/10* (2006.01)

(52) U.S. Cl. .................... 800/285; 800/295; 800/300.1; 435/468; 435/320.1; 536/23.6; 536/23.1

(58) Field of Classification Search ........................ None
See application file for complete search history.

(56) References Cited

U.S. PATENT DOCUMENTS

| 5,593,963 A | 1/1997 | Van Ooijen et al. | |
|---|---|---|---|
| 6,197,561 B1 * | 3/2001 | Martino-Catt et al. | 800/278 |
| 6,476,212 B1 * | 11/2002 | Lalgudi et al. | 536/23.6 |

FOREIGN PATENT DOCUMENTS

| WO | WO 99/05298 A1 | 2/1999 |
|---|---|---|
| WO | WO 99/55879 A1 | 11/1999 |
| WO | WO 00/04166 A2 | 1/2000 |
| WO | WO 01/04147 A2 | 1/2001 |
| WO | WO 03/000905 A2 | 1/2003 |

OTHER PUBLICATIONS

Seeds et al 2007 Advan. Enzyme. Regule. 47:10-25.*
Hatzack et al., High-performance thin-layer chromatography method for inositol phosphate analysis, Journal of Chromatography B (1999) 736:221-229.
Loewus et al., myo-Inositol metabolism in plants, Plant Science (2000) 150:1-19.
Majerus et al., The Role of Phosphatases in Inositol Signaling Reactions, J. Biol. Chem. (1999) 274(16):10669-10672.
Odom et al., A Role for Nuclear Inositol 1,4,5-Trisphosphate Kinase in Transcriptional Control, Science (2000) 287:2026-2029.
Saiardi et al., Synthesis of diphosphoinositol pentakisphosphate by a newly identified family of higher inositol polyphosphate kinases, Current Biology (1999) 9:1323-1326.
Saiardi et al., Inositol polyphosphate multikinase (ArgRIII) determines nuclear mRNA export in *Saccharomyces cerevisiae*, FEBS Letters (2000) 468:28-32.
Spencer et al., Separation of Higher Insitol Phosphates by Polyethyleneimine-Cellulose Thin-Layer Chromatography and by Dowex Chloride Column Chromatography, Methods in Inositide Research (1990) pp. 39-43.
Clandinin et al., NCBI Accession No. AF045613, *Caenorhabditis elegans* inositol trisphosphate 3-kinase form 3 (LFE-2) mRNA, complete cds (1998).
Dubois et al., NCBI Accession No. X05328, Yeast ARGRIII gene for arginine metabolism regulation (1993).
Huang et al., NCBI Accession No. S54640, KCS1 protein—yeast (*Saccharomyces cerevisiae*) (2000).
Takazawa et al., NCBI Accession No. X54938, Human mRNA for inositol 1,4,5-triphosphate 3-kinase (1991).
Takazawa et al., NCBI Accession No. X56917, Rat mRNA for inositol 1,4,5-triphosphate 3-kinase (1991).
Takazawa et al., NCBI Accession No. X57206, *H. sapiens* mRNA for 1D-myo-inositol-trisphosphate 3-kinase B isoenzyme (1992).
Thomas et al., NCBI Accession No. X74227, *R. norvegicus* mRNA for IP3 3-kinase (1999).
Wilson et al., NCBI Accession No. AF080173, *Arabidopsis thaliana* inositol 1,3,4-triphosphate 5/6-kinase mRNA, complete cds (1998).
Xu et al., NCBI Accession No. AJ404678, *Arabidopsis thaliana* mRNA for putative inositol hexaphosphate kinase (ip6K gene) (2000).
Xue et al., NCBI Accession No. AJ001753, *Arabidopsis thaliana* mRNA for inositol 1,3,4-Trisphosphate 5/6 Kinase (1998).
Cutler et al., Cellulose synthesis: Cloning in silico, Current Biology (1997) 7:R108-R111.
Favery et al., *KOJAK* encodes a cellulose synthase-like protein required for root hair cell morphogenesis in *Arabidopsis*, Genes & Development (2001) 15(1):79-89.
Pear et al., Higher plants contain homologs of the bacterial *celA* genes encoding the catalytic subunit of cellulose synthase, Proc. Natl. Acad. Sci. USA (1996) 93:12637-12642.
Walbot, V., Database EMBL Accession No. AI657474, Endosperm cDNA library from Schmidt lab Zea mays cDNA, mRNA sequence (1999).
Yamada et al., Database EMBL Accession No. AF360180, *Arabidopsis thaliana* putative cellulose synthase catalytic subunit (At3g03050) mRNA, complete cds (2001).
Yamada et al., Database EMOL Accession No. Q9M9M4, Putative cellulose synthase catalytic subunit (Cellulose synthase-like CSLD3) (Cellulose synthase-like protein) (2000).
Bohnert et al., Adaptations to Environmental Stresses, The Plant Cell (1995) 7:1099-1111.
Bowie et al., Deciphering the Message in Protein Sequences: Tolerance to Amino Acid Substitutions, Science (1990) 247:1306-1310.
McConnell et al., Role of *PHABULOSA* and *PHAVOLUTA* in determining radial patterning in shoots, Nature (2001) 411:709-713.

* cited by examiner

*Primary Examiner*—Anne Marie Grunberg
*Assistant Examiner*—Brent Page
(74) *Attorney, Agent, or Firm*—Pioneer Hi-Bred International, Inc.; Kathryn K. Lappegard

(57) ABSTRACT

This invention relates to newly identified polynucleotides and polypeptides in the phytic acid biosynthetic pathway, variants and derivatives of same; methods for making the polynucleotides, polypeptides, variants, derivatives and antagonists. In particular the invention relates to polynucleotides and polypeptides of the inositol polyphosphate kinase gene family. In particular this invention relates to using the newly identified polynucleotides and polypeptides to modulate phytic acid biosynthesis in such a way as to decrease phytate and/or increase non-phytate phosphorous in plants.

10 Claims, No Drawings

SEQUENCE LISTING

<160> NUMBER OF SEQ ID NOS: 39

<210> SEQ ID NO 1
<211> LENGTH: 1169
<212> TYPE: DNA
<213> ORGANISM: Zea mays
<220> FEATURE:
<221> NAME/KEY: CDS
<222> LOCATION: (84)...(806)

<400> SEQUENCE: 1

```
aaaatctctt tctccgctgc gctgcaaacc caccgcttcc accatcgcca ctcgtcaccc      60
cttgctccca tagtccccat acc atg ccc gac ctc cac ccg ccg gag cac caa     113
                        Met Pro Asp Leu His Pro Pro Glu His Gln
                          1               5                  10 gtc gcc ggt cac cgc gcc tcc gcc agc aag ctg ggc ccg ctc atc gac       161
Val Ala Gly His Arg Ala Ser Ala Ser Lys Leu Gly Pro Leu Ile Asp
                 15                  20                  25 ggc tcc ggc ctc ttc tac aag ccg ctc cag gcc ggc gac cgt ggg gag       209
Gly Ser Gly Leu Phe Tyr Lys Pro Leu Gln Ala Gly Asp Arg Gly Glu
             30                  35                  40 cac gag gtc gcc ttc tat gag gcg ttc tcc gcc cac gcc gcc gtc ccg       257
His Glu Val Ala Phe Tyr Glu Ala Phe Ser Ala His Ala Ala Val Pro
         45                  50                  55 gcc cgc atc cga gac acc ttc ttc ccc cgg ttc cac ggc acg cga ctc       305
Ala Arg Ile Arg Asp Thr Phe Phe Pro Arg Phe His Gly Thr Arg Leu
     60                  65                  70 ctc ccc acc gag gcg cag ccc ggg gag ccg cat ccg cac ctc gtc ctc       353
Leu Pro Thr Glu Ala Gln Pro Gly Glu Pro His Pro His Leu Val Leu
 75                  80                  85                  90 gac gac ctc ctc gcg ggg ttt gag gcg ccc tgc gtc gca gac atc aag       401
Asp Asp Leu Leu Ala Gly Phe Glu Ala Pro Cys Val Ala Asp Ile Lys
                 95                 100                 105 atc ggc gcc atc acg tgg cca ccg agt tcg ccg gag ccc tac atc gcc       449
Ile Gly Ala Ile Thr Trp Pro Pro Ser Ser Pro Glu Pro Tyr Ile Ala
             110                 115                 120 aag tac ctc gcc aag gac cgc ggg acc acg agc gtt ctg ctc gga ttc       497
Lys Tyr Leu Ala Lys Asp Arg Gly Thr Thr Ser Val Leu Leu Gly Phe
         125                 130                 135 cgc gtc ttg cgt ccg agt cgt cgg ccc cga ggg cgc cgt gtg gcg gac       545
Arg Val Leu Arg Pro Ser Arg Arg Pro Arg Gly Arg Arg Val Ala Asp
     140                 145                 150 gga gcg ccc gga ggt gaa ggc tat gga cac cgt cgg cgt ccg ccg cgt       593
Gly Ala Pro Gly Gly Glu Gly Tyr Gly His Arg Arg Arg Pro Pro Arg
155                 160                 165                 170 gct ccg gcg cta cgt gtc atc cgc ttg ccg acg agg gga tgg act gcg       641
Ala Pro Ala Leu Arg Val Ile Arg Leu Pro Thr Arg Gly Trp Thr Ala
                 175                 180                 185 cgc tcg cgg cgg cgg tgt acg gag gaa aag gtg gag tct tgt cac agc       689
Arg Ser Arg Arg Arg Cys Thr Glu Glu Lys Val Glu Ser Cys His Ser
             190                 195                 200 tgc gcg agc tca agg cat ggt tgg agg agc aga ctc tgt tcc act tct       737
Cys Ala Ser Ser Arg His Gly Trp Arg Ser Arg Leu Cys Ser Thr Ser
         205                 210                 215 act cgg cgt cga ttc ttc tgg gct atg atg ctg ctg cag tcg cag cag       785
Thr Arg Arg Arg Phe Phe Trp Ala Met Met Leu Leu Gln Ser Gln Gln
     220                 225                 230 gcg gag gtg ggg gtg ggg taa cagtgaagct ggtggacttt gcccatgtgg          836
Ala Glu Val Gly Val Gly  *
235                 240 ccgagggtga tggggtgatt gaccacaact tcctgggcga gctctgctag ctgatcaagt    896
tcgtttctga cattgttcca gagactcctt agacgcagcc tttgggtcct tcttaagaga    956
ggatcctgac attttttgatt tgataacaaa ggaagcactt tcagctgcaa aaaaagaaag    1016
cagcagtgag gatgaagatg acagtagtga ggaaagttcg gatgatgagc aacaaaagt     1076 tgaagaaaag aaggctccaa aagtatcaga aaacattgga tctgaggatg aatcttctga    1136
```
agacgagagt gataaagaca gtgaagagcc tca                                    1169

<210> SEQ ID NO 2
<211> LENGTH: 240
<212> TYPE: PRT
<213> ORGANISM: Zea mays

<400> SEQUENCE: 2

Met Pro Asp Leu His Pro Pro Glu His Gln Val Ala Gly His Arg Ala
1               5                   10                  15

Ser Ala Ser Lys Leu Gly Pro Leu Ile Asp Gly Ser Gly Leu Phe Tyr
            20                  25                  30

Lys Pro Leu Gln Ala Gly Asp Arg Gly Glu His Glu Val Ala Phe Tyr
        35                  40                  45

Glu Ala Phe Ser Ala His Ala Ala Val Pro Ala Arg Ile Arg Asp Thr
50                  55                  60

Phe Phe Pro Arg Phe His Gly Thr Arg Leu Leu Pro Thr Glu Ala Gln
65                  70                  75                  80

Pro Gly Glu Pro His Pro His Leu Val Leu Asp Asp Leu Leu Ala Gly
                85                  90                  95

Phe Glu Ala Pro Cys Val Ala Asp Ile Lys Ile Gly Ala Ile Thr Trp
            100                 105                 110

Pro Pro Ser Ser Pro Glu Pro Tyr Ile Ala Lys Tyr Leu Ala Lys Asp
        115                 120                 125

Arg Gly Thr Thr Ser Val Leu Leu Gly Phe Arg Val Leu Arg Pro Ser
    130                 135                 140

Arg Arg Pro Arg Gly Arg Arg Val Ala Asp Gly Ala Pro Gly Gly Glu
145                 150                 155                 160

Gly Tyr Gly His Arg Arg Arg Pro Pro Arg Ala Pro Ala Leu Arg Val
                165                 170                 175

Ile Arg Leu Pro Thr Arg Gly Trp Thr Ala Arg Ser Arg Arg Arg Cys
            180                 185                 190

Thr Glu Glu Lys Val Glu Ser Cys His Ser Cys Ala Ser Ser Arg His
        195                 200                 205

Gly Trp Arg Ser Arg Leu Cys Ser Thr Ser Thr Arg Arg Phe Phe
    210                 215                 220

Trp Ala Met Met Leu Leu Gln Ser Gln Gln Ala Glu Val Gly Val Gly
225                 230                 235                 240

<210> SEQ ID NO 3
<211> LENGTH: 923
<212> TYPE: DNA
<213> ORGANISM: Zea mays
<220> FEATURE:
<221> NAME/KEY: CDS
<222> LOCATION: (53)...(736)

<400> SEQUENCE: 3
accgcttcca ccatcgccac tcgtcacccc ttgctcccat agtccccata cc atg ccc    58
                                                          Met Pro
                                                          1 gac ctc cac ccg ccg gag cac caa gtc gcc ggt cac cgc gcc tcc gcc    106
Asp Leu His Pro Pro Glu His Gln Val Ala Gly His Arg Ala Ser Ala
        5                   10                  15 agc aag ccg ggc ccg ctc atc gac ggc tcc ggc ctc ttc tac aag ccg    154
Ser Lys Pro Gly Pro Leu Ile Asp Gly Ser Gly Leu Phe Tyr Lys Pro
    20                  25                  30 ctc cag gcc ggc gac cgt ggg gag cac gag gtc gct ttc tat gag gcg    202

-continued

```
Leu Gln Ala Gly Asp Arg Gly Glu His Glu Val Ala Phe Tyr Glu Ala
 35                  40                  45                  50 ttc tcc gcc cac gcc gcc gtc ccg gcc cgc atc cga gac acc ttc ttc    250
Phe Ser Ala His Ala Ala Val Pro Ala Arg Ile Arg Asp Thr Phe Phe
             55                  60                  65 ccc cgg ttc cac ggc acg cga ctc ctc ccc acc gag gcg cag ccc ggg    298
Pro Arg Phe His Gly Thr Arg Leu Leu Pro Thr Glu Ala Gln Pro Gly
             70                  75                  80 gag ccg cat ccg cac ctc gtc ctc gac gac ctc ctc gcg gga ttt gag    346
Glu Pro His Pro His Leu Val Leu Asp Asp Leu Leu Ala Gly Phe Glu
         85                  90                  95 gcg ccc tgc gtc gca gac atc aag atc ggc gcc atc acg tgg cca ccg    394
Ala Pro Cys Val Ala Asp Ile Lys Ile Gly Ala Ile Thr Trp Pro Pro
    100                 105                 110 agt tcg ccg gag ccc tac atc gcc aag tgc ctc gcc atg gac cgc ggg    442
Ser Ser Pro Glu Pro Tyr Ile Ala Lys Cys Leu Ala Met Asp Arg Gly
115                 120                 125                 130 acc acg agc gtt ctg ctc gga ttc cgc gtc tcc ggc gtc cga gtc gtc    490
Thr Thr Ser Val Leu Leu Gly Phe Arg Val Ser Gly Val Arg Val Val
                135                 140                 145 gtc ccc gag ggc gcc gtg tgg cgg acg gag cgc ccg gag gtg aag gct    538
Val Pro Glu Gly Ala Val Trp Arg Thr Glu Arg Pro Glu Val Lys Ala
            150                 155                 160 atg gac acc gtc ggc gtc cgc cgc gtg ctc cgg cgc tac gtg tca tcc    586
Met Asp Thr Val Gly Val Arg Arg Val Leu Arg Arg Tyr Val Ser Ser
        165                 170                 175 gct tgc cga cga ggg gat gga ctg cgc gct cgc ggc ggc ggt gta cgg    634
Ala Cys Arg Arg Gly Asp Gly Leu Arg Ala Arg Gly Gly Gly Val Arg
    180                 185                 190 agg aaa agg tgg agt ctt gtc act gct gcg cga gct caa ggc gtg gtt    682
Arg Lys Arg Trp Ser Leu Val Thr Ala Ala Arg Ala Gln Gly Val Val
195                 200                 205                 210 cga gga gca gcc tct gtt cca ctt cta ctc ggc gtc gat tct tct ggg    730
Arg Gly Ala Ala Ser Val Pro Leu Leu Leu Gly Val Asp Ser Ser Gly
                215                 220                 225 cta tga tgctgctgca gtcgcagcag gcggaggtgg gggtggggta acagtgaagc    786
Leu * tggtggactt tgcccatgtg gccgagggtg atggggtgat tgaccacaac ttcctgggcg    846
ggctctgcta gctgatcaag ttcgtttctg acattgttcc agagactcct cagacgcagc    906
ctttgggtcc ttcttaa                                                    923
```

<210> SEQ ID NO 4
<211> LENGTH: 227
<212> TYPE: PRT
<213> ORGANISM: Zea mays

<400> SEQUENCE: 4

```
Met Pro Asp Leu His Pro Pro Glu His Gln Val Ala Gly His Arg Ala
 1               5                  10                  15

Ser Ala Ser Lys Pro Gly Pro Leu Ile Asp Gly Ser Gly Leu Phe Tyr
             20                  25                  30

Lys Pro Leu Gln Ala Gly Asp Arg Gly Glu His Glu Val Ala Phe Tyr
         35                  40                  45

Glu Ala Phe Ser Ala His Ala Ala Val Pro Ala Arg Ile Arg Asp Thr
     50                  55                  60

Phe Phe Pro Arg Phe His Gly Thr Arg Leu Leu Pro Thr Glu Ala Gln
 65                  70                  75                  80
```

```
Pro Gly Glu Pro His Pro His Leu Val Leu Asp Asp Leu Leu Ala Gly
            85                  90                  95

Phe Glu Ala Pro Cys Val Ala Asp Ile Lys Ile Gly Ala Ile Thr Trp
            100                 105                 110

Pro Pro Ser Ser Pro Glu Pro Tyr Ile Ala Lys Cys Leu Ala Met Asp
            115                 120                 125

Arg Gly Thr Thr Ser Val Leu Leu Gly Phe Arg Val Ser Gly Val Arg
130                 135                 140

Val Val Val Pro Glu Gly Ala Val Trp Arg Thr Glu Arg Pro Glu Val
145                 150                 155                 160

Lys Ala Met Asp Thr Val Gly Val Arg Arg Val Leu Arg Arg Tyr Val
            165                 170                 175

Ser Ser Ala Cys Arg Arg Gly Asp Gly Leu Arg Ala Arg Gly Gly Gly
            180                 185                 190

Val Arg Arg Lys Arg Trp Ser Leu Val Thr Ala Ala Arg Ala Gln Gly
            195                 200                 205

Val Val Arg Gly Ala Ala Ser Val Pro Leu Leu Gly Val Asp Ser
210                 215                 220

Ser Gly Leu
225

<210> SEQ ID NO 5
<211> LENGTH: 923
<212> TYPE: DNA
<213> ORGANISM: Zea mays
<220> FEATURE:
<221> NAME/KEY: CDS
<222> LOCATION: (53)...(922)

<400> SEQUENCE: 5
accgcttcca ccatcgccac tcgtcacccc ttgctcccat agtccccata cc atg ccc    58
                                                           Met Pro
                                                             1 gac ctc cac ccg ccg gag cac caa gtc gcc ggt cac cgc gcc tcc gcc    106
Asp Leu His Pro Pro Glu His Gln Val Ala Gly His Arg Ala Ser Ala
        5                   10                  15 agc aag ccg ggc ccg ctc atc gac ggc tcc ggc ctc ttc tac aag ccg    154
Ser Lys Pro Gly Pro Leu Ile Asp Gly Ser Gly Leu Phe Tyr Lys Pro
    20                  25                  30 ctc cag gcc ggc gac cgt ggg gag cac gag gtc gct ttc tat gag gcg    202
Leu Gln Ala Gly Asp Arg Gly Glu His Glu Val Ala Phe Tyr Glu Ala
35                  40                  45                  50 ttc tcc gcc cac gcc gcc gtc ccg gcc cgc atc cga gac acc ttc ttc    250
Phe Ser Ala His Ala Ala Val Pro Ala Arg Ile Arg Asp Thr Phe Phe
            55                  60                  65 ccc cgg ttc cac ggc acg cga ctc ctc ccc acc gag gcg cag ccc ggg    298
Pro Arg Phe His Gly Thr Arg Leu Leu Pro Thr Glu Ala Gln Pro Gly
        70                  75                  80 gag ccg cat ccg cac ctc gtc ctc gac gac ctc ctc gcg gga ttt gag    346
Glu Pro His Pro His Leu Val Leu Asp Asp Leu Leu Ala Gly Phe Glu
    85                  90                  95 gcg ccc tgc gtc gca gac atc aag atc ggc gcc atc acg tgg cca ccg    394
Ala Pro Cys Val Ala Asp Ile Lys Ile Gly Ala Ile Thr Trp Pro Pro
100                 105                 110 agt tcg ccg gag ccc tac atc gcc aag tgc ctc gcc atg gac cgc ggg    442
Ser Ser Pro Glu Pro Tyr Ile Ala Lys Cys Leu Ala Met Asp Arg Gly
115                 120                 125                 130 acc acg agc gtt ctg ctc gga ttc cgc gtc tcc ggc gtc cga gtc gtc    490
Thr Thr Ser Val Leu Leu Gly Phe Arg Val Ser Gly Val Arg Val Val
```

-continued

```
                 135                 140                 145
ggc ccc gag ggc gcc gtg tgg cgg acg gag cgc ccg gag gtg aag gcc    538
Gly Pro Glu Gly Ala Val Trp Arg Thr Glu Arg Pro Glu Val Lys Ala
            150                 155                 160 atg gac acc gcc ggc gtc cgc cgc gtg ctc cgg cgc tac gtg tca tcc    586
Met Asp Thr Ala Gly Val Arg Arg Val Leu Arg Arg Tyr Val Ser Ser
        165                 170                 175 gtt gcc gac gag ggg atg gac tgt gcg ctc gcc gcg gcg gtg tac gga    634
Val Ala Asp Glu Gly Met Asp Cys Ala Leu Ala Ala Ala Val Tyr Gly
    180                 185                 190 gga aaa ggt gga gtc ttg tca cag ctg cgc gag ctc aag gcg tgg ttc    682
Gly Lys Gly Gly Val Leu Ser Gln Leu Arg Glu Leu Lys Ala Trp Phe
195                 200                 205                 210 gag gag cag act ctg ttc cac ttc tac tcg gcg tcg att ctt ctg ggc    730
Glu Glu Gln Thr Leu Phe His Phe Tyr Ser Ala Ser Ile Leu Leu Gly
                215                 220                 225 tat gat gct gct gca gtc gca gca ggc gga ggt ggg ggt ggg gtg acg    778
Tyr Asp Ala Ala Ala Val Ala Ala Gly Gly Gly Gly Gly Gly Val Thr
            230                 235                 240 gtg aag ctg gtg gac ttt gcc cat gtg gcc gag ggt gat ggg gtg att    826
Val Lys Leu Val Asp Phe Ala His Val Ala Glu Gly Asp Gly Val Ile
        245                 250                 255 gac cac aac ttc ctg ggc ggg ctc tgc tcg ctg atc aag ttc gtt tct    874
Asp His Asn Phe Leu Gly Gly Leu Cys Ser Leu Ile Lys Phe Val Ser
    260                 265                 270 gac att gtt cca gag act cct cag acg cag cct ttg ggt cct tct taa    922
Asp Ile Val Pro Glu Thr Pro Gln Thr Gln Pro Leu Gly Pro Ser  *
275                 280                 285 g                                                                  923
```

210> SEQ ID NO 6
<211> LENGTH: 289
<212> TYPE: PRT
<213> ORGANISM: Zea mays

<400> SEQUENCE: 6

Met Pro Asp Leu His Pro Glu His Gln Val Ala Gly His Arg Ala
 1               5                  10                  15

Ser Ala Ser Lys Pro Gly Pro Leu Ile Asp Gly Ser Gly Leu Phe Tyr
            20                  25                  30

Lys Pro Leu Gln Ala Gly Asp Arg Gly Glu His Glu Val Ala Phe Tyr
        35                  40                  45

Glu Ala Phe Ser Ala His Ala Ala Val Pro Ala Arg Ile Arg Asp Thr
    50                  55                  60

Phe Phe Pro Arg Phe His Gly Thr Arg Leu Leu Pro Thr Glu Ala Gln
65                  70                  75                  80

Pro Gly Glu Pro His Pro His Leu Val Leu Asp Asp Leu Leu Ala Gly
                85                  90                  95

Phe Glu Ala Pro Cys Val Ala Asp Ile Lys Ile Gly Ala Ile Thr Trp
            100                 105                 110

Pro Pro Ser Ser Pro Glu Pro Tyr Ile Ala Lys Cys Leu Ala Met Asp
        115                 120                 125

Arg Gly Thr Thr Ser Val Leu Leu Gly Phe Arg Val Ser Gly Val Arg
    130                 135                 140

Val Val Gly Pro Glu Gly Ala Val Trp Arg Thr Glu Arg Pro Glu Val
145                 150                 155                 160

Lys Ala Met Asp Thr Ala Gly Val Arg Arg Val Leu Arg Arg Tyr Val

```
                165                 170                 175
Ser Ser Val Ala Asp Glu Gly Met Asp Cys Ala Leu Ala Ala Val
            180                 185                 190

Tyr Gly Gly Lys Gly Gly Val Leu Ser Gln Leu Arg Glu Leu Lys Ala
            195                 200                 205

Trp Phe Glu Glu Gln Thr Leu Phe His Phe Tyr Ser Ala Ser Ile Leu
    210                 215                 220

Leu Gly Tyr Asp Ala Ala Val Ala Ala Gly Gly Gly Gly Gly
225                 230                 235                 240

Val Thr Val Lys Leu Val Asp Phe Ala His Val Ala Glu Gly Asp Gly
            245                 250                 255

Val Ile Asp His Asn Phe Leu Gly Gly Leu Cys Ser Leu Ile Lys Phe
        260                 265                 270

Val Ser Asp Ile Val Pro Glu Thr Pro Gln Thr Gln Pro Leu Gly Pro
        275                 280                 285

Ser

<210> SEQ ID NO 7
<211> LENGTH: 1344
<212> TYPE: DNA
<213> ORGANISM: Zea mays
<220> FEATURE:
<221> NAME/KEY: CDS
<222> LOCATION: (52)...(921)

<400> SEQUENCE: 7
gcacgaggtc agtccgtcac ccctcgcgcc catagtcccc ttccccatac c atg tcc        57
                                                         Met Ser
                                                           1 gac ctc cac ccg ccg gag cac caa gtc gcc ggc cac cgc gcc tcc gcc        105
Asp Leu His Pro Pro Glu His Gln Val Ala Gly His Arg Ala Ser Ala
        5                   10                  15 agc aag ctg ggc ccg ctc atc gac ggc tcc ggc ctc ttc tac aag ccg        153
Ser Lys Leu Gly Pro Leu Ile Asp Gly Ser Gly Leu Phe Tyr Lys Pro
    20                  25                  30 ctc cag gcc ggc gac cgt ggg gag cac gag gtc gcc ttc tat gag gcg        201
Leu Gln Ala Gly Asp Arg Gly Glu His Glu Val Ala Phe Tyr Glu Ala
35                  40                  45                  50 ttc tcc gcc cac gcc gcc gtc ccg gcc cgc atc cga gac acc ttc ttc        249
Phe Ser Ala His Ala Ala Val Pro Ala Arg Ile Arg Asp Thr Phe Phe
                55                  60                  65 ccc cgg ttc cac ggc acg cga ctc ctc ccc acc gag gcg cag ccc ggg        297
Pro Arg Phe His Gly Thr Arg Leu Leu Pro Thr Glu Ala Gln Pro Gly
            70                  75                  80 gag ccg cat cct cac ctc gtc ctc gac gac ctc ctc gcg ggg ttt cag        345
Glu Pro His Pro His Leu Val Leu Asp Asp Leu Leu Ala Gly Phe Gln
        85                  90                  95 gcg ccc tgc gtc gca gac atc aag atc ggc gcc atc acg tgg cca ccg        393
Ala Pro Cys Val Ala Asp Ile Lys Ile Gly Ala Ile Thr Trp Pro Pro
    100                 105                 110 agt tcg ccg gag ccc tac atc gcc aag tgc ctc gcc aag gac cgc ggg        441
Ser Ser Pro Glu Pro Tyr Ile Ala Lys Cys Leu Ala Lys Asp Arg Gly
115                 120                 125                 130 acc acg agc gtt ctg ctc gga ttc cgc gtc tcc ggc gtc cga gtc gtc        489
Thr Thr Ser Val Leu Leu Gly Phe Arg Val Ser Gly Val Arg Val Val
                135                 140                 145 ggc ccc gag ggc gcc gtg tgg cgg acg gag cgc ccg gag gtg aag gcc        537
Gly Pro Glu Gly Ala Val Trp Arg Thr Glu Arg Pro Glu Val Lys Ala
            150                 155                 160
```

```
atg gac acc gcc ggc gtc cgc cgc gtg ctc cgg cgc tac gtg tca tcc    585
Met Asp Thr Ala Gly Val Arg Arg Val Leu Arg Arg Tyr Val Ser Ser
    165                 170                 175 gtt gcc gac gag ggg atg gac tgt gcg ctc gcc gcg gcg gtg tac gga    633
Val Ala Asp Glu Gly Met Asp Cys Ala Leu Ala Ala Ala Val Tyr Gly
180                 185                 190 gga aaa ggt gga gtc ttg tca cag ctg cgc gag ctc aag gcg tgg ttc    681
Gly Lys Gly Gly Val Leu Ser Gln Leu Arg Glu Leu Lys Ala Trp Phe
195                 200                 205                 210 gag gag cag act ctg ttc cac ttc tac tcg gcg tcg att ctt ctg ggc    729
Glu Glu Gln Thr Leu Phe His Phe Tyr Ser Ala Ser Ile Leu Leu Gly
                215                 220                 225 tat gat gct gct gca gtc gca gca ggc gga gat ggg ggt ggg gtg acg    777
Tyr Asp Ala Ala Ala Val Ala Ala Gly Gly Asp Gly Gly Gly Val Thr
            230                 235                 240 gtg aag ctg gtg gac ttt gcc cat gtg gcc gag ggt gat ggg gtg att    825
Val Lys Leu Val Asp Phe Ala His Val Ala Glu Gly Asp Gly Val Ile
        245                 250                 255 gac cac aac ttc ctg ggc ggg ctc tgc tcg ctg atc aag ttc gtt tct    873
Asp His Asn Phe Leu Gly Gly Leu Cys Ser Leu Ile Lys Phe Val Ser
    260                 265                 270 gac att gtt ccg gag act cct cat acg cag cct ttg ggt cct tct taa    921
Asp Ile Val Pro Glu Thr Pro His Thr Gln Pro Leu Gly Pro Ser  *
275                 280                 285 gagaggatcc tggcatttcg atttgataac aaagccctac aagttttgtc tggaaaaaga    981
agcgcctccg agttgtgctg ggtgtggaga tctgagacgg tcgtcggccc acttggttgc   1041
cttgcctttg ccttgcctgc aaacatacgg caacctgctc ctttttttcgc aaccccttac   1101
ttccgaagaa actttttttt tcccactttg ggggttcgat tacgttggat ctggtttgtg   1161
ccactcggtc agaggttgta agcatggagg gaggcgtgtt gatccggcaa ctgtgtcagt   1221
cttttgcgctg cctgccgttt ctgcatggct tttgcctgct gcgatccgat gtgtactgga   1281
gatcgtagtg atggacgtct ctacctccaa acgaatccgt ccgataaaaa aaaaaaaaa   1341
aaa                                                                 1344

<210> SEQ ID NO 8
<211> LENGTH: 289
<212> TYPE: PRT
<213> ORGANISM: Zea mays

<400> SEQUENCE: 8

Met Ser Asp Leu His Pro Glu His Gln Val Ala Gly His Arg Ala
1               5                   10                  15

Ser Ala Ser Lys Leu Gly Pro Leu Ile Asp Gly Ser Gly Leu Phe Tyr
                20                  25                  30

Lys Pro Leu Gln Ala Gly Asp Arg Gly Glu His Glu Val Ala Phe Tyr
            35                  40                  45

Glu Ala Phe Ser Ala His Ala Ala Val Pro Ala Arg Ile Arg Asp Thr
        50                  55                  60

Phe Phe Pro Arg Phe His Gly Thr Arg Leu Leu Pro Thr Glu Ala Gln
65                  70                  75                  80

Pro Gly Glu Pro His Pro His Leu Val Leu Asp Asp Leu Leu Ala Gly
                85                  90                  95

Phe Gln Ala Pro Cys Val Ala Asp Ile Lys Ile Gly Ala Ile Thr Trp
            100                 105                 110

Pro Pro Ser Ser Pro Glu Pro Tyr Ile Ala Lys Cys Leu Ala Lys Asp
```

-continued

```
                    115                 120                 125
Arg Gly Thr Thr Ser Val Leu Leu Gly Phe Arg Val Ser Gly Val Arg
    130                 135                 140

Val Val Gly Pro Glu Gly Ala Val Trp Arg Thr Glu Arg Pro Glu Val
145                 150                 155                 160

Lys Ala Met Asp Thr Ala Gly Val Arg Arg Val Leu Arg Arg Tyr Val
                165                 170                 175

Ser Ser Val Ala Asp Glu Gly Met Asp Cys Ala Leu Ala Ala Ala Val
            180                 185                 190

Tyr Gly Gly Lys Gly Val Leu Ser Gln Leu Arg Glu Leu Lys Ala
        195                 200                 205

Trp Phe Glu Glu Gln Thr Leu Phe His Phe Tyr Ser Ala Ser Ile Leu
    210                 215                 220

Leu Gly Tyr Asp Ala Ala Val Ala Ala Gly Gly Asp Gly Gly Gly
225                 230                 235                 240

Val Thr Val Lys Leu Val Asp Phe Ala His Val Ala Glu Gly Asp Gly
                245                 250                 255

Val Ile Asp His Asn Phe Leu Gly Gly Leu Cys Ser Leu Ile Lys Phe
            260                 265                 270

Val Ser Asp Ile Val Pro Glu Thr Pro His Thr Gln Pro Leu Gly Pro
        275                 280                 285

Ser

<210> SEQ ID NO 9
<211> LENGTH: 1105
<212> TYPE: DNA
<213> ORGANISM: Glycine max
<220> FEATURE:
<221> NAME/KEY: CDS
<222> LOCATION: (12)...(851)

<400> SEQUENCE: 9
gcacgagaaa a atg ctc aag atc ccg gag cac cag gtg gcc ggg cac aag      50
            Met Leu Lys Ile Pro Glu His Gln Val Ala Gly His Lys
              1               5                  10 gcc aag gac gga atc ctg ggc cca ctc gtc gac gat ttt gga aaa ttc       98
Ala Lys Asp Gly Ile Leu Gly Pro Leu Val Asp Asp Phe Gly Lys Phe
 15                  20                  25 tac aag ccc ctc cag acc aac aaa gac gac gac acc cgc ggc tcc acc      146
Tyr Lys Pro Leu Gln Thr Asn Lys Asp Asp Asp Thr Arg Gly Ser Thr
 30                  35                  40                  45 gaa ctc tcc ttt tac acc tct ctc gcc gcc gcc gcc cac gac tac tcc      194
Glu Leu Ser Phe Tyr Thr Ser Leu Ala Ala Ala Ala His Asp Tyr Ser
                 50                  55                  60 atc cgc tcc ttc ttc ccc gcc ttt cac ggc acc cgc ctc ctg gac gcc      242
Ile Arg Ser Phe Phe Pro Ala Phe His Gly Thr Arg Leu Leu Asp Ala
             65                  70                  75 tcc gac ggc tcc ggt ccc cac cct cac ctg gtc ctg gag gac ctc ctc      290
Ser Asp Gly Ser Gly Pro His Pro His Leu Val Leu Glu Asp Leu Leu
         80                  85                  90 tgc ggc tac tcc aaa ccc tcc gtc atg gac gta aag atc ggc tcc aga      338
Cys Gly Tyr Ser Lys Pro Ser Val Met Asp Val Lys Ile Gly Ser Arg
     95                 100                 105 acc tgg cac ctg gga gac tcc gag gac tac atc tgc aag tgc ctg aag      386
Thr Trp His Leu Gly Asp Ser Glu Asp Tyr Ile Cys Lys Cys Leu Lys
110                 115                 120                 125 aag gac aga gag tcc tct agc ttg ccc ttg ggt ttc aga atc tcg gga      434
Lys Asp Arg Glu Ser Ser Ser Leu Pro Leu Gly Phe Arg Ile Ser Gly
```

```
gtc aag gac tct atc tcc tcc tgg gaa cct acc agg aaa tct ctc cag      482
Val Lys Asp Ser Ile Ser Ser Trp Glu Pro Thr Arg Lys Ser Leu Gln
            145                 150                 155 tgt cta tcc gcc cat ggt gtt gca ctt gtt ctc aac aag ttc gtt tcc      530
Cys Leu Ser Ala His Gly Val Ala Leu Val Leu Asn Lys Phe Val Ser
        160                 165                 170 tct aat aat atc aac cat gat gat cat cat ccc gat tgc gct ttc gca      578
Ser Asn Asn Ile Asn His Asp Asp His His Pro Asp Cys Ala Phe Ala
    175                 180                 185 acg gag gtc tac ggc gcc gtt ttg gag cgc ttg cag aag ctc aag gac      626
Thr Glu Val Tyr Gly Ala Val Leu Glu Arg Leu Gln Lys Leu Lys Asp
190                 195                 200                 205 tgg ttc gag gtt cag acg gtg tat cac ttc tat tct tgt tct gtt ctt      674
Trp Phe Glu Val Gln Thr Val Tyr His Phe Tyr Ser Cys Ser Val Leu
                210                 215                 220 gtg gtg tac gag aag gat cta ggg aaa ggg aaa gct acc aac cct ctg      722
Val Val Tyr Glu Lys Asp Leu Gly Lys Gly Lys Ala Thr Asn Pro Leu
            225                 230                 235 gtc aaa ctc gtt gac ttt gca cac gtg gtg gac gga aac ggt gtc att      770
Val Lys Leu Val Asp Phe Ala His Val Val Asp Gly Asn Gly Val Ile
        240                 245                 250 gat cac aac ttc ttg ggt ggc ctt tgt tcc ttc atc aag ttc ctc aag      818
Asp His Asn Phe Leu Gly Gly Leu Cys Ser Phe Ile Lys Phe Leu Lys
    255                 260                 265 gat atc cta gca gta gca tgt ctt cac aag tga ctgattttca tcgagttaat   871
Asp Ile Leu Ala Val Ala Cys Leu His Lys *
270                 275 cttattccta tcagaaaata attatgcttg aattagtgtc gcagactaac tgtttgaagt    931
actgtcagaa acaaataat aatatggact gagaggcaat cttgttctgc taaactccct     991
ttcaagttgc tgtcagatac tagccgtccc ttttccttt tcatattctg tcaaagtgag   1051
tcatttaata ataataacaa tgtccttcaa ctccaaaaaa aaaaaaaaaa aaaa         1105
```

<210> SEQ ID NO 10
<211> LENGTH: 279
<212> TYPE: PRT
<213> ORGANISM: Glycine max

<400> SEQUENCE: 10

```
Met Leu Lys Ile Pro Glu His Gln Val Ala Gly His Lys Ala Lys Asp
 1               5                  10                  15

Gly Ile Leu Gly Pro Leu Val Asp Asp Phe Gly Lys Phe Tyr Lys Pro
            20                  25                  30

Leu Gln Thr Asn Lys Asp Asp Thr Arg Gly Ser Thr Glu Leu Ser
        35                  40                  45

Phe Tyr Thr Ser Leu Ala Ala Ala His Asp Tyr Ser Ile Arg Ser
    50                  55                  60

Phe Phe Pro Ala Phe His Gly Thr Arg Leu Leu Asp Ala Ser Asp Gly
65                  70                  75                  80

Ser Gly Pro His Pro His Leu Val Leu Glu Asp Leu Leu Cys Gly Tyr
                85                  90                  95

Ser Lys Pro Ser Val Met Asp Val Lys Ile Gly Ser Arg Thr Trp His
            100                 105                 110

Leu Gly Asp Ser Glu Asp Tyr Ile Cys Lys Cys Leu Lys Lys Asp Arg
        115                 120                 125

Glu Ser Ser Ser Leu Pro Leu Gly Phe Arg Ile Ser Gly Val Lys Asp
```

```
                130                 135                 140
Ser Ile Ser Ser Trp Glu Pro Thr Arg Lys Ser Leu Gln Cys Leu Ser
145                 150                 155                 160

Ala His Gly Val Ala Leu Val Leu Asn Lys Phe Val Ser Ser Asn Asn
                165                 170                 175

Ile Asn His Asp Asp His His Pro Asp Cys Ala Phe Ala Thr Glu Val
                180                 185                 190

Tyr Gly Ala Val Leu Glu Arg Leu Gln Lys Leu Lys Asp Trp Phe Glu
            195                 200                 205

Val Gln Thr Val Tyr His Phe Tyr Ser Cys Ser Val Leu Val Val Tyr
    210                 215                 220

Glu Lys Asp Leu Gly Lys Gly Lys Ala Thr Asn Pro Leu Val Lys Leu
225                 230                 235                 240

Val Asp Phe Ala His Val Val Asp Gly Asn Gly Val Ile Asp His Asn
                245                 250                 255

Phe Leu Gly Gly Leu Cys Ser Phe Ile Lys Phe Leu Lys Asp Ile Leu
            260                 265                 270

Ala Val Ala Cys Leu His Lys
        275

<210> SEQ ID NO 11
<211> LENGTH: 1195
<212> TYPE: DNA
<213> ORGANISM: Eucalyptus grandis
<220> FEATURE:
<221> NAME/KEY: CDS
<222> LOCATION: (116)...(1048)

<400> SEQUENCE: 11
gcaccagctt cttggagtag ttgcccatca gcgtggattt tcattttagt ccatctggct      60
gtgatcaatc gaatctgagt aagtttggag aattttttcg cacatcagat acacc atg     118
                                                                 Met
                                                                   1 ctc aag gtc ccg gat cat caa gtc gcc ggt cac cgg gga gac ggg gga      166
Leu Lys Val Pro Asp His Gln Val Ala Gly His Arg Gly Asp Gly Gly
            5                   10                  15 aag ctg ggg cca ctg gtg gat gat tcg ggc cgc ttc tat aag cct ctc      214
Lys Leu Gly Pro Leu Val Asp Asp Ser Gly Arg Phe Tyr Lys Pro Leu
        20                  25                  30 cag agc gat cat cgc gga gac acg gaa gtg gcc ttt tac gag tca ttc      262
Gln Ser Asp His Arg Gly Asp Thr Glu Val Ala Phe Tyr Glu Ser Phe
    35                  40                  45 tat tcc aat acc gag atc cca ggt cac att cgc aaa ttc ttt cct gcg      310
Tyr Ser Asn Thr Glu Ile Pro Gly His Ile Arg Lys Phe Phe Pro Ala
50                  55                  60                  65 ttt cac gga act aag act att gag gcg tct gat gga tcg ggt cct caa      358
Phe His Gly Thr Lys Thr Ile Glu Ala Ser Asp Gly Ser Gly Pro Gln
                70                  75                  80 cct cac ctg gtt ctg gag gat ctc gtc tcg ggt cgc acg aac cca tct      406
Pro His Leu Val Leu Glu Asp Leu Val Ser Gly Arg Thr Asn Pro Ser
            85                  90                  95 ctc atg gac atc aag act gga tcc aga aca tgg tat ccg gag gcc tct      454
Leu Met Asp Ile Lys Thr Gly Ser Arg Thr Trp Tyr Pro Glu Ala Ser
        100                 105                 110 gag gag tac atc caa aag tgc tta gag aaa gat cga aat agc aca agc      502
Glu Glu Tyr Ile Gln Lys Cys Leu Glu Lys Asp Arg Asn Ser Thr Ser
    115                 120                 125 gtt tca ttg ggt ttt agg att tct ggg cta agg gta tat caa aat agc      550
```

```
Val Ser Leu Gly Phe Arg Ile Ser Gly Leu Arg Val Tyr Gln Asn Ser
130                 135                 140                 145 gaa gct gga ttt tgg caa cct gag aag aag gtt gtt tat agc ttt aat      598
Glu Ala Gly Phe Trp Gln Pro Glu Lys Lys Val Val Tyr Ser Phe Asn
                150                 155                 160 gcg gac ggt gtc agg tcg gct ctg agg aag ttt gtt tct tcc aac ttg      646
Ala Asp Gly Val Arg Ser Ala Leu Arg Lys Phe Val Ser Ser Asn Leu
            165                 170                 175 tct ctg ggt cca aat gtg gat ccg gat tgt ttg tat gca tca aaa gtt      694
Ser Leu Gly Pro Asn Val Asp Pro Asp Cys Leu Tyr Ala Ser Lys Val
        180                 185                 190 tac tgt cac cgg ggt gga att ttg gca caa ttg ctt cag ctg aag gaa      742
Tyr Cys His Arg Gly Gly Ile Leu Ala Gln Leu Leu Gln Leu Lys Glu
    195                 200                 205 tgg ttt gag gtt cag acg aat tat cac ttc tat tct tgt tca ctc att      790
Trp Phe Glu Val Gln Thr Asn Tyr His Phe Tyr Ser Cys Ser Leu Ile
210                 215                 220                 225 atc tta tat gac agg gag tct gct ttg gac ggc tgt gca cac ccg aaa      838
Ile Leu Tyr Asp Arg Glu Ser Ala Leu Asp Gly Cys Ala His Pro Lys
                230                 235                 240 gtt aaa ctg gtg gac ttt gca cat gtg atg gat ggc cac ggc gtg atc      886
Val Lys Leu Val Asp Phe Ala His Val Met Asp Gly His Gly Val Ile
            245                 250                 255 gat cac aac ttc ttg ggt ggc ctc tgt tct gta atc aag ttt ata cgt      934
Asp His Asn Phe Leu Gly Gly Leu Cys Ser Val Ile Lys Phe Ile Arg
        260                 265                 270 gac att gct gat gaa gat aac aag tgt gca aag tgc gaa gtc aat ctt      982
Asp Ile Ala Asp Glu Asp Asn Lys Cys Ala Lys Cys Glu Val Asn Leu
275                 280                 285 gga ttg aaa gaa aat ggc ttc tat aag agc agc acg gaa cca gag ctt     1030
Gly Leu Lys Glu Asn Gly Phe Tyr Lys Ser Ser Thr Glu Pro Glu Leu
290                 295                 300                 305 gat cac gag gcc tgc tag tggaaactgg agaataactg cattcatgca            1078
Asp His Glu Ala Cys *
                310 ttcctgcatt cctgctctga caagtggttc agaatgggta taataacagt ctattttagt   1138 caaaaaaaaa aaaaaaaaaa aaaaaaaaaa aaaaaaaaaa aaaaaaaaaa aaaaaaa      1195

<210> SEQ ID NO 12
<211> LENGTH: 310
<212> TYPE: PRT
<213> ORGANISM: Eucalyptus grandis

<400> SEQUENCE: 12

Met Leu Lys Val Pro Asp His Gln Val Ala Gly His Arg Gly Asp Gly
1               5                   10                  15

Gly Lys Leu Gly Pro Leu Val Asp Asp Ser Gly Arg Phe Tyr Lys Pro
            20                  25                  30

Leu Gln Ser Asp His Arg Gly Asp Thr Glu Val Ala Phe Tyr Glu Ser
        35                  40                  45

Phe Tyr Ser Asn Thr Glu Ile Pro Gly His Ile Arg Lys Phe Phe Pro
    50                  55                  60

Ala Phe His Gly Thr Lys Thr Ile Glu Ala Ser Asp Gly Ser Gly Pro
65                  70                  75                  80

Gln Pro His Leu Val Leu Glu Asp Leu Val Ser Gly Arg Thr Asn Pro
                85                  90                  95

Ser Leu Met Asp Ile Lys Thr Gly Ser Arg Thr Trp Tyr Pro Glu Ala
            100                 105                 110
```

```
Ser Glu Glu Tyr Ile Gln Lys Cys Leu Glu Lys Asp Arg Asn Ser Thr
        115                 120                 125

Ser Val Ser Leu Gly Phe Arg Ile Ser Gly Leu Arg Val Tyr Gln Asn
    130                 135                 140

Ser Glu Ala Gly Phe Trp Gln Pro Glu Lys Lys Val Val Tyr Ser Phe
145                 150                 155                 160

Asn Ala Asp Gly Val Arg Ser Ala Leu Arg Lys Phe Val Ser Ser Asn
                165                 170                 175

Leu Ser Leu Gly Pro Asn Val Asp Pro Asp Cys Leu Tyr Ala Ser Lys
                180                 185                 190

Val Tyr Cys His Arg Gly Gly Ile Leu Ala Gln Leu Leu Gln Leu Lys
            195                 200                 205

Glu Trp Phe Glu Val Gln Thr Asn Tyr His Phe Tyr Ser Cys Ser Leu
        210                 215                 220

Ile Ile Leu Tyr Asp Arg Glu Ser Ala Leu Asp Gly Cys Ala His Pro
225                 230                 235                 240

Lys Val Lys Leu Val Asp Phe Ala His Val Met Asp Gly His Gly Val
                245                 250                 255

Ile Asp His Asn Phe Leu Gly Gly Leu Cys Ser Val Ile Lys Phe Ile
                260                 265                 270

Arg Asp Ile Ala Asp Glu Asp Asn Lys Cys Ala Lys Cys Glu Val Asn
            275                 280                 285

Leu Gly Leu Lys Glu Asn Gly Phe Tyr Lys Ser Thr Glu Pro Glu
        290                 295                 300

Leu Asp His Glu Ala Cys
305                 310

<210> SEQ ID NO 13
<211> LENGTH: 1020
<212> TYPE: DNA
<213> ORGANISM: Parthenium argentatum
<220> FEATURE:
<221> NAME/KEY: CDS
<222> LOCATION: (21)...(908)

<400> SEQUENCE: 13
gcacgagaac ttcttcagac atg ctc aag gcc cca gat cat cag gtt gct gga     53
                     Met Leu Lys Ala Pro Asp His Gln Val Ala Gly
                      1               5                  10 cat gaa gct ggg ctc ggg aag ctt ggc cca ctc att gat gat tca ggc    101
His Glu Ala Gly Leu Gly Lys Leu Gly Pro Leu Ile Asp Asp Ser Gly
             15                  20                  25 cgg ttt tac aaa cca ctg cag ggt gat aac cgt ggg tca gaa gaa gta    149
Arg Phe Tyr Lys Pro Leu Gln Gly Asp Asn Arg Gly Ser Glu Glu Val
         30                  35                  40 gcc ttt tat gaa tca ttt tct tct aac aat aat att cca gaa cac ata    197
Ala Phe Tyr Glu Ser Phe Ser Ser Asn Asn Asn Ile Pro Glu His Ile
     45                  50                  55 cgc aaa ttc ttt cct ata tat tat ggc acc aaa atc atg aag gca tcc    245
Arg Lys Phe Phe Pro Ile Tyr Tyr Gly Thr Lys Ile Met Lys Ala Ser
 60                  65                  70                  75 act ggc tct gac cat cct cac atg gtg ttg caa gat ctt aca tca gct    293
Thr Gly Ser Asp His Pro His Met Val Leu Gln Asp Leu Thr Ser Ala
                 80                  85                  90 cat gtc aac cca tct gta atg gac atc aaa atc ggg tcc aga aca tgg    341
His Val Asn Pro Ser Val Met Asp Ile Lys Ile Gly Ser Arg Thr Trp
             95                 100                 105
```

```
gcg cca gaa gct tcc gag gcg tac att gca aaa tgc tta aaa aag gat        389
Ala Pro Glu Ala Ser Glu Ala Tyr Ile Ala Lys Cys Leu Lys Lys Asp
        110                 115                 120 agg gaa agc aca agt att cca ttg gga ttc agg atc tcc ggg ctg caa        437
Arg Glu Ser Thr Ser Ile Pro Leu Gly Phe Arg Ile Ser Gly Leu Gln
    125                 130                 135 gtc tat atc gat gat ggg tca ggg ttt tat aag cct cat aga aat tac        485
Val Tyr Ile Asp Asp Gly Ser Gly Phe Tyr Lys Pro His Arg Asn Tyr
140                 145                 150                 155 atg cgt aaa acc ggc cca gct gat gtt aga cta ctt ctt agg aaa ttt        533
Met Arg Lys Thr Gly Pro Ala Asp Val Arg Leu Leu Leu Arg Lys Phe
                160                 165                 170 gtt tct tct aac ccg tct gca gag atg gaa atg cgc aca ggc cta ggc        581
Val Ser Ser Asn Pro Ser Ala Glu Met Glu Met Arg Thr Gly Leu Gly
            175                 180                 185 ccg gat tgt tct tta gca tct ttt gtt tat ggt ggg cct aat ggg ata        629
Pro Asp Cys Ser Leu Ala Ser Phe Val Tyr Gly Gly Pro Asn Gly Ile
        190                 195                 200 tta gct caa ctg atg gaa ttg aag aca tgg ttt gaa gat caa aca att        677
Leu Ala Gln Leu Met Glu Leu Lys Thr Trp Phe Glu Asp Gln Thr Ile
    205                 210                 215 tac cac ttc tat gct tgt tct ttt ttg ttc atc ttt gaa aag agg ttg        725
Tyr His Phe Tyr Ala Cys Ser Phe Leu Phe Ile Phe Glu Lys Arg Leu
220                 225                 230                 235 gtg tta aaa ggt gct cgg tca aac gca gaa gtc aaa ctt att gat ttt        773
Val Leu Lys Gly Ala Arg Ser Asn Ala Glu Val Lys Leu Ile Asp Phe
                240                 245                 250 gct cat gtt aca gat ggt aat ggt gtt att gat cac aat ttc ttg ggt        821
Ala His Val Thr Asp Gly Asn Gly Val Ile Asp His Asn Phe Leu Gly
            255                 260                 265 ggg ctc tgt tct ttg ata aag ttc att tct gac ata ctt tcg gag aca        869
Gly Leu Cys Ser Leu Ile Lys Phe Ile Ser Asp Ile Leu Ser Glu Thr
        270                 275                 280 aaa gat tgt aat ggt aca aac ggt cag gtt gaa ctt tga aactctcttc        918
Lys Asp Cys Asn Gly Thr Asn Gly Gln Val Glu Leu  *
    285                 290                 295 ttgttgcttt tcttcaataa tttatcatga cagtgtttaa ttgtaaagat attcgcttac      978
cggaatatat cttggttatg agtgaaaaaa aaaaaaaaaa aa                        1020
```

<210> SEQ ID NO 14
<211> LENGTH: 295
<212> TYPE: PRT
<213> ORGANISM: Parthenium argentatum

<400> SEQUENCE: 14

```
Met Leu Lys Ala Pro Asp His Gln Val Ala Gly His Glu Ala Gly Leu
1               5                   10                  15

Gly Lys Leu Gly Pro Leu Ile Asp Asp Ser Gly Arg Phe Tyr Lys Pro
                20                  25                  30

Leu Gln Gly Asp Asn Arg Gly Ser Glu Glu Val Ala Phe Tyr Glu Ser
            35                  40                  45

Phe Ser Ser Asn Asn Asn Ile Pro Glu His Ile Arg Lys Phe Phe Pro
        50                  55                  60

Ile Tyr Tyr Gly Thr Lys Ile Met Lys Ala Ser Thr Gly Ser Asp His
65                  70                  75                  80

Pro His Met Val Leu Gln Asp Leu Thr Ser Ala His Val Asn Pro Ser
                85                  90                  95

Val Met Asp Ile Lys Ile Gly Ser Arg Thr Trp Ala Pro Glu Ala Ser
```

-continued

```
                100                 105                 110
Glu Ala Tyr Ile Ala Lys Cys Leu Lys Lys Asp Arg Glu Ser Thr Ser
            115                 120                 125

Ile Pro Leu Gly Phe Arg Ile Ser Gly Leu Gln Val Tyr Ile Asp Asp
        130                 135                 140

Gly Ser Gly Phe Tyr Lys Pro His Arg Asn Tyr Met Arg Lys Thr Gly
145                 150                 155                 160

Pro Ala Asp Val Arg Leu Leu Arg Lys Phe Val Ser Ser Asn Pro
                165                 170                 175

Ser Ala Glu Met Glu Met Arg Thr Gly Leu Gly Pro Asp Cys Ser Leu
            180                 185                 190

Ala Ser Phe Val Tyr Gly Gly Pro Asn Gly Ile Leu Ala Gln Leu Met
        195                 200                 205

Glu Leu Lys Thr Trp Phe Glu Asp Gln Thr Ile Tyr His Phe Tyr Ala
    210                 215                 220

Cys Ser Phe Leu Phe Ile Phe Glu Lys Arg Leu Val Leu Lys Gly Ala
225                 230                 235                 240

Arg Ser Asn Ala Glu Val Lys Leu Ile Asp Phe Ala His Val Thr Asp
                245                 250                 255

Gly Asn Gly Val Ile Asp His Asn Phe Leu Gly Gly Leu Cys Ser Leu
            260                 265                 270

Ile Lys Phe Ile Ser Asp Ile Leu Ser Glu Thr Lys Asp Cys Asn Gly
        275                 280                 285

Thr Asn Gly Gln Val Glu Leu
    290                 295

<210> SEQ ID NO 15
<211> LENGTH: 899
<212> TYPE: DNA
<213> ORGANISM: Zea mays
<220> FEATURE:
<221> NAME/KEY: CDS
<222> LOCATION: (89)...(424)

<400> SEQUENCE: 15
gccccaaaat ctctttctcc gctgcgccgc aaacccaccg cttccaccat cgccacccgt      60
caccccttgc tcccatagtc cccatacc atg ccc gac ctc cac ccg ccg gag       112
                                 Met Pro Asp Leu His Pro Pro Glu
                                   1               5 cac caa gtc gcc ggt cac cgc gcc tcc gcc agc aag ctg ggc cca ctc      160
His Gln Val Ala Gly His Arg Ala Ser Ala Ser Lys Leu Gly Pro Leu
     10                  15                  20 atc gac ggc tct ggc ctc ttc tac aag ccg ctc cag gcc ggc gac cgt      208
Ile Asp Gly Ser Gly Leu Phe Tyr Lys Pro Leu Gln Ala Gly Asp Arg
 25                  30                  35                  40 ggg gag cac gag gtc gcc ttc tat gag gcg ttc tcc gcc cac gcc gcc      256
Gly Glu His Glu Val Ala Phe Tyr Glu Ala Phe Ser Ala His Ala Ala
                 45                  50                  55 gtc ccg gcc cgc atc cga gac acc ttc ttc ccc cgg ttc cac ggc acg      304
Val Pro Ala Arg Ile Arg Asp Thr Phe Phe Pro Arg Phe His Gly Thr
             60                  65                  70 cga ctc ctc ccc acc gag gcg cag ccc ggg gag ccg cat ccg tac ctc      352
Arg Leu Leu Pro Thr Glu Ala Gln Pro Gly Glu Pro His Pro Tyr Leu
         75                  80                  85 gtc ctc gac gac ctc ctc gcg ggg ttt gag gcg ccc tgc gtc gca gac      400
Val Leu Asp Asp Leu Leu Ala Gly Phe Glu Ala Pro Cys Val Ala Asp
     90                  95                 100
```

-continued

```
atc aag atc ggt gcc atc acg tga ccatgagcga tctgctcgga ttccacgtct    454
Ile Lys Ile Gly Ala Ile Thr  *
105             110 ccggcgtccg agtcgtcggc cccgagggcg ccgtgtggcg gacggagcgc cctgaggtga    514
aggctatgga cattgtcggc gtccgccgcg tgctccggcg ctgcatgtca tccgcttgcc    574
ggcgagggga tggactgcgc gctcgcggcg gcggtgtacg gaggaaaagg tggagtcttg    634
tcacagctgc gcgagctcaa ggcgtggttc gaggggcaga ctctgttcca cttctactcg    694
gcgtcgattc ttctgggcta tgatgctgct gcagtcgcag caggcggagg tgggggtggg    754
gtaacagtga agctggtgga ccttgcccat gtggccgagg tgatggggt gattgaccac     814 aacttcctgg gcgggctctg ctagctgatc aagtttgttt ctgacattgt tccagagact    874
ccttagacgc agcaagggcg aattc                                          899
```

<210> SEQ ID NO 16
<211> LENGTH: 111
<212> TYPE: PRT
<213> ORGANISM: Zea mays
<400> SEQUENCE: 16

```
Met Pro Asp Leu His Pro Pro Glu His Gln Val Ala Gly His Arg Ala
1               5                   10                  15

Ser Ala Ser Lys Leu Gly Pro Leu Ile Asp Gly Ser Gly Leu Phe Tyr
            20                  25                  30

Lys Pro Leu Gln Ala Gly Asp Arg Gly Glu His Glu Val Ala Phe Tyr
        35                  40                  45

Glu Ala Phe Ser Ala His Ala Ala Val Pro Ala Arg Ile Arg Asp Thr
    50                  55                  60

Phe Phe Pro Arg Phe His Gly Thr Arg Leu Leu Pro Thr Glu Ala Gln
65                  70                  75                  80

Pro Gly Glu Pro His Pro Tyr Leu Val Leu Asp Asp Leu Leu Ala Gly
                85                  90                  95

Phe Glu Ala Pro Cys Val Ala Asp Ile Lys Ile Gly Ala Ile Thr
            100                 105                 110
```

<210> SEQ ID NO 17
<211> LENGTH: 643
<212> TYPE: DNA
<213> ORGANISM: Zea mays
<220> FEATURE:
<221> NAME/KEY: misc_feature
<222> LOCATION: (1)...(643)
<223> OTHER INFORMATION: n = A, T, C or G
<400> SEQUENCE: 17

```
ggccgtccct gnttttgtta accaccccgc cccaaaatct ctttctccgc tgcgctgcaa     60
acccaccgct tccaccatcg ccactcgtca cccctgctc ccatagtccc cataccatgc     120
ccgacctcca cccgccggag caccaagtcg ccggtcaccg cgcctccgcc agcaagctgg    180
gcccgctcat cgacggctcc ggcctcttct acaagccgct ccaggccggc gaccgtgggg    240
agcacgaggt cgccttctat gaggcgttct ccgcccacgc cgncgtcccg gcccgcatcc    300
gagacaccct tcttcccccgg ttccacggca cgcgactcct ccccaccgag gcgcagcccg    360
gggagccgca tccgcacctc gtcctcgacg acctcctcgc ggggtttgag gcgccctgcg    420
tcgcagacat caagatcggc gccatcacgt ggcaccgag ttcgccggag ccctacatcg     480
ncaagtacct ngccaaggac cgcgggacca cgagcgttct gctcggattc cgcgtcttgc    540
```

```
gtccgagtcg tcggccccga gggcgccgtg tggcggacgg agcgcccgg gggtgaangc      600 tatggacacc cgtcggngnc cggcgngtgc ttcgggngct acg                       643

<210> SEQ ID NO 18
<211> LENGTH: 519
<212> TYPE: DNA
<213> ORGANISM: Zea mays
<220> FEATURE:
<221> NAME/KEY: misc_feature
<222> LOCATION: (1)...(519)
<223> OTHER INFORMATION: n = A, T, C, or G

<400> SEQUENCE: 18
ggtacggang aaaangtgga gtcttgtcac agctgcgcga gctcaangcg tggttcgagg      60
ggcagactct gttccacttc tactcggcgt cgattcttct gggctatgat gctgctgcag     120
tcgcagcagg cggangtggg ggtggggtaa cagtgaagct ggtggacttt gcccatgtgg     180
ccgagggtga tgggtgatt gaccacaact tcctgggcgg gctctgctan ctgatcaagt      240
ttgtttctga cattgttcca gagactcctc agacgcagcc tttgggtcct tcttaagaaa     300
agatcctggc atttcgatt tgataacaaa ggaancactt tcagctgcca aaaaaaanc       360 accagtgaag atgaaaataa cattattgag gaaagttccg atnataaccc accanattna     420
aaaaaaaaag gtcccaaatt tccgaaaatn tggatcttaa gaataatctc ctgaaaacan     480
aattataaaa cgtgaaaacc ccggctncnt catttacnc                            519

<210> SEQ ID NO 19
<211> LENGTH: 353
<212> TYPE: DNA
<213> ORGANISM: Zea mays
<220> FEATURE:
<221> NAME/KEY: misc_feature
<222> LOCATION: (1)...(353)
<223> OTHER INFORMATION: n = A, T, C, or G

<400> SEQUENCE: 19
ctcaaggcat ggttggagga gcagactctg ttccacttct actcggcgtc gattcttctg     60
ggctatgatg ctgctgcagt cgcancaggc ggaggtgggg gtggggtaac agtgaagctg     120
gtggactttg cccatgtggc cgagggtgat ggggttgatt tgaccacaac ttcctgggcg     180
agctctgcta gctgatcaag ttccgtttct tgacattgtt ccaganactc cttagacgcc     240
agcctttggg tccttcctta aaaaagatc cctgacnttt ttgatttgat tacnaaggaa      300
acactttcca cttgccnaaa aaaaagccc ntgaggatta aaaattaac ntt              353

<210> SEQ ID NO 20
<211> LENGTH: 3416
<212> TYPE: DNA
<213> ORGANISM: Zea mays
<220> FEATURE:
<221> NAME/KEY: CDS
<222> LOCATION: (72)...(407)

<400> SEQUENCE: 20
ccacgcgtcc ggcaaaccca ccgcttccac catcgccacc cgtcacccct tgctcccata      60
gtccccatac c atg ccc gac ctc cac ccg ccg gag cac caa gtc gcc ggt      110
            Met Pro Asp Leu His Pro Pro Glu His Gln Val Ala Gly
              1               5                  10 cac cgc gcc tcc gcc agc aag ctg ggc cca ctc atc gac gac tct ggc      158
His Arg Ala Ser Ala Ser Lys Leu Gly Pro Leu Ile Asp Asp Ser Gly
         15                  20                  25
```

```
ctc ttc tac aag ccg ctc cag gcc ggc gac cgt ggg gag cac gag gtc      206
Leu Phe Tyr Lys Pro Leu Gln Ala Gly Asp Arg Gly Glu His Glu Val
 30                  35                  40                  45 gcc ttc tat gag gcg ttc tcc gcc cac gcc gcc gtc ccg gcc cgc atc      254
Ala Phe Tyr Glu Ala Phe Ser Ala His Ala Ala Val Pro Ala Arg Ile
                 50                  55                  60 cga gac acc ttc ttc ccc cgg ttc cac ggc acg cga ctc ctc ccc acc      302
Arg Asp Thr Phe Phe Pro Arg Phe His Gly Thr Arg Leu Leu Pro Thr
                     65                  70                  75 gag gcg cag ccc ggg gag ccg cat ccg cac ctc gtc ctc gac gac ctc      350
Glu Ala Gln Pro Gly Glu Pro His Pro His Leu Val Leu Asp Asp Leu
             80                  85                  90 ctc gcg ggg ttt gag gcg ccc tgc gtc gca gac atc aag atc ggt gcc      398
Leu Ala Gly Phe Glu Ala Pro Cys Val Ala Asp Ile Lys Ile Gly Ala
 95                 100                 105 atc acg tga ccacgagcgt tctgctcgga ttccgcgtct ccggcgtccg              447
Ile Thr *
110 agtcgtcggc ccgaggggcg ccgtgtggcg gacggagcgc ccggaggtga aggctatgga     507
cattgtcggc gtccgccgcg tgctccggcg ctacgtgtca tccgcttgcc gacgagggga     567
tggactgcgc gctcgcggcg gcggtgtacg gaggaaaagg tggagtcttg tcacagctgc     627
gcgagctcaa ggcgtggttc gaggggcaga ctctgttcca cttctactcg gcgtcgattc     687
ttctgggcta tgatgctgct gcagtcgcag caggcggagg tgggggtggg gtaacagtga     747
agctggtgga ctttgcccat gtggccgagg gtgatgggt gattgaccac aacttcctgg     807
gcgggctctg ctagctgatc aagtttgttt ctgacattgt tccagagact cctcagacgc     867
agcctttggg tccttcttaa gagaggatcc tggcatttc gatttgataa caaaggaagc      927
actttcagct gcaaaaaaag aaagcagcag tgaggatgaa gatgacagta gtgaggaaag     987
ttcggatgat gagccaacaa aagttgaaga aagaaggct ccaaaagtat cagaaaatat     1047
tggatctgag gatgaatctt ctgaagacaa gagtgataaa gacagtgaag agcctcaggc    1107
atgccatcat ttaacacctc aggcatgcca tcattttgt ttcacaactc aaaagtaaag    1167
gaaaacagta aagtatgca ggcagtatga gggacacaca tagtttactg aaactcctt     1227
acacagacac atacacaccg tgttcactga acattcaga tttcactaaa ctgcaacttc    1287
tccaaacaaa cactatctgc ggctcggtca agtaacgagc ctcggctcgg ctcgctcctc    1347
tagcgagcct aaaagtcgg ctcggttcgg cgagccaacg agcctgacca taagcatgaa    1407
atcagtctcc aaaatataat ataaagtctc aaaataatt taagtgacac gtcttaaatt   1467
agtaaaataa atatatatca tataatatag aaaataagtt aattttgtac agtaatctaa   1527
aaaatataaa ttaatcatct atttagtacc tataatatat gttaattaaa atttatataa   1587
caaaaatgtt gttgtttgag ccagctcgcg agctgaactg gctcgctctg gctcgctctt   1647
ttattgagcc agaaaaaact ctgctcgagc ttgttctaag cacagtttct ggatcggagg   1707
agcatccccg cctaggtctc tgcagccatg gttcgcggat cgctcggcaa gcttgcatcg   1767
cgcgccctct ccgtcgccgg gagatggcag caccagcagc tccgccgcct caacatccac   1827
gagtaccagg gcgcggagtt gatgggtaaa tacgggatca acgtgcccag gggcgcggcg   1887
gctgggtccg tacatgaggt caaggacgcc ttgaagaaca tgttcccag cgagaaagag    1947
atagttgtta aaagtcaaat ccttgctggt ggccgagggc tgggaacttt caaaagcgga   2007
ctgcaaggtg gtgtccatat tgttaaggct gaggaagctg aattgattgc aagtaaaatg    2067
ttaggccaga ttctgataac gaaacaaact ggtccagagg gaaagattgt gagcaaggtc    2127
```

-continued

```
tacttgtgtg agaaactatc tcttactaat gagatgtact tgccatcac ccttgatagg      2187 aaaactgctg gtccgctcat tattgcttgc agcaagggag gaaaacacta tagttgacct     2247
caatgttcaa aggatggcca gggctacatc atcttgttgt tgacgggttc cgtgtgttca     2307
atcgccgagc agaaagccag gaacagaact taggcgttgg cgattggcat ctccctcccc     2367
taagccatgg ccaccgggcg gcccgtacga ctcgtgctgg atgcctccct cctcctcgac     2427
ccctcctcca ccagggaggc ggcggcggtg gctctgcggc ccggggtaga ggagctgttg     2487
cggcggttgc gctactccaa cctgaatgtg gcaatctgct atgcagaggg catgccaact     2547
aatgagatgc tctacttatc tacattatta ttacatccct ctgaagttgt atcttcagaa     2607
gttcacattg acagtatttg cttcctcttg ccatacttac ccatcatggc ccatggggtg     2667
tctatcttat catgccatct tcaaagaatg gcatcatgtt aacaaaaatg aatgagaaat     2727
cagtcatttc taatggaaag tcaggctttc ttgaaaaggt cgcaagctca cacttgtttg     2787
gctctatagc acttcttgcg aaaagtggga atctttctct aactgaatta atgttagaat     2847
ggagccaaac aagtttatgt ttttatgcga cttcaagagt tgacaaaggt ttaagttctg     2907
agctccagaa tcagaattgg agagttcttt ctgtagctaa tgaatgtagc atagaggttc     2967
ctggtgtttt aaatgttcaa aggcttcagc agttgcttct cacccttgct actctaataa     3027
aagggaacta tgtgactcat ctgttctggt gattggatat ataatgaaaa tattctgtga     3087
ggaagacttc gcaaggagat gtggttctgt cacttatgtg accgttgtcg tgtatggaga     3147
cgtgtatgga gacgaggaca agccagcgct tataatgttt acagagatgt ggttctgtga     3207
ctgttgccgt gtactcaggc tttatttcaa caagatttaa atatgagatg tagagtgatt     3267
gatgtacatc acttcactaa tcatgaaatc tgtagaaggc gaaactacta gccatatatg     3327
atatgcataa tccgtgtggt aaacattatc aatatcacac aaattatttc taatgggttt     3387
tgaattatca aaaaaaaaaa aaaaaaaaa                                        3416
```

<210> SEQ ID NO 21
<211> LENGTH: 111
<212> TYPE: PRT
<213> ORGANISM: Zea mays

<400> SEQUENCE: 21

```
Met Pro Asp Leu His Pro Pro Glu His Gln Val Ala Gly His Arg Ala
1               5                   10                  15

Ser Ala Ser Lys Leu Gly Pro Leu Ile Asp Asp Ser Gly Leu Phe Tyr
            20                  25                  30

Lys Pro Leu Gln Ala Gly Asp Arg Gly Glu His Glu Val Ala Phe Tyr
        35                  40                  45

Glu Ala Phe Ser Ala His Ala Ala Val Pro Ala Arg Ile Arg Asp Thr
    50                  55                  60

Phe Phe Pro Arg Phe His Gly Thr Arg Leu Leu Pro Thr Glu Ala Gln
65                  70                  75                  80

Pro Gly Glu Pro His Pro His Leu Val Leu Asp Asp Leu Leu Ala Gly
                85                  90                  95

Phe Glu Ala Pro Cys Val Ala Asp Ile Lys Ile Gly Ala Ile Thr
            100                 105                 110
```

<210> SEQ ID NO 22
<211> LENGTH: 1448
<212> TYPE: DNA
<213> ORGANISM: Parthenium argentatum

<220> FEATURE:
<221> NAME/KEY: CDS
<222> LOCATION: (52)...(1020)

<400> SEQUENCE: 22

```
gcacgaggca cactcaatgg ctccgatgct cagaggccaa cggagggtac c atg ctg       57
                                                         Met Leu
                                                         1 cca gct cca gct gtt cct aat ggc acg ggt gct ccg ctt aag gac gaa      105
Pro Ala Pro Ala Val Pro Asn Gly Thr Gly Ala Pro Leu Lys Asp Glu
        5                  10                  15 cct tcc aac ccc gat cag gcg cag cac cag cct gac gag cgc gtt caa      153
Pro Ser Asn Pro Asp Gln Ala Gln His Gln Pro Asp Glu Arg Val Gln
 20                  25                  30 cac ttc atc ctt ctt gaa gac ctt act gct ggc atg aca agg cct tgt      201
His Phe Ile Leu Leu Glu Asp Leu Thr Ala Gly Met Thr Arg Pro Cys
 35                  40                  45                  50 gtc tta gac ttg aag atg ggt acg cgc cag tat ggt gtg gaa gcc gat      249
Val Leu Asp Leu Lys Met Gly Thr Arg Gln Tyr Gly Val Glu Ala Asp
             55                  60                  65 gag aag aaa cag cgg tct caa cgg cgc aag tgt cag atg acc acc agt      297
Glu Lys Lys Gln Arg Ser Gln Arg Arg Lys Cys Gln Met Thr Thr Ser
         70                  75                  80 gct caa ctc ggc gtg cga gtc tgc ggt atg caa att tgg aac gcc aag      345
Ala Gln Leu Gly Val Arg Val Cys Gly Met Gln Ile Trp Asn Ala Lys
     85                  90                  95 acc cag agc tac atc ttc gag gac aag tac ttc ggt cga gat ctg aaa      393
Thr Gln Ser Tyr Ile Phe Glu Asp Lys Tyr Phe Gly Arg Asp Leu Lys
100                 105                 110 gca gga aaa gaa ttt cag gac gcg ctt aag cgc ttt ttt tgg gat ggg      441
Ala Gly Lys Glu Phe Gln Asp Ala Leu Lys Arg Phe Phe Trp Asp Gly
115                 120                 125                 130 acg agc tac aaa gca gca aac aga cac ata ccc gtc ata ttg gag aag      489
Thr Ser Tyr Lys Ala Ala Asn Arg His Ile Pro Val Ile Leu Glu Lys
            135                 140                 145 atc agc caa ctg gaa cgc atg ata cga aaa ctt cca gga tac aga ttc      537
Ile Ser Gln Leu Glu Arg Met Ile Arg Lys Leu Pro Gly Tyr Arg Phe
        150                 155                 160 tac gcg agt agt ttg ttg atg ctc tat gat cgt ggg gac ggt gag tcg      585
Tyr Ala Ser Ser Leu Leu Met Leu Tyr Asp Arg Gly Asp Gly Glu Ser
    165                 170                 175 aag gag aaa gac gca gca ccc tct tta cct aac ggc ttg tcg aac ccg      633
Lys Glu Lys Asp Ala Ala Pro Ser Leu Pro Asn Gly Leu Ser Asn Pro
180                 185                 190 agc aac gaa gac gtt tca aca ata cca tct gga ctt aca tca cca ggg      681
Ser Asn Glu Asp Val Ser Thr Ile Pro Ser Gly Leu Thr Ser Pro Gly
195                 200                 205                 210 ccg aca gtc gct tct aaa ccg tca ccc aag aag cac gga gag atc aag      729
Pro Thr Val Ala Ser Lys Pro Ser Pro Lys Lys His Gly Glu Ile Lys
            215                 220                 225 ctg aaa att gtc gac ttt gcc aac tgc gtg act gca gaa gac cct cta      777
Leu Lys Ile Val Asp Phe Ala Asn Cys Val Thr Ala Glu Asp Pro Leu
        230                 235                 240 cca gac gac tta cct tgt cca cct gaa aat ccc gac ggc atc gat aga      825
Pro Asp Asp Leu Pro Cys Pro Pro Glu Asn Pro Asp Gly Ile Asp Arg
    245                 250                 255 ggg tac ctc cgt ggc ctc cga tca cta cgc ctc tac ttc caa cgc att      873
Gly Tyr Leu Arg Gly Leu Arg Ser Leu Arg Leu Tyr Phe Gln Arg Ile
260                 265                 270 tgg aat gac atc aac gag gaa tgg gtc gaa cga ggc gag ggc gag ggc      921
```

```
Trp Asn Asp Ile Asn Glu Glu Trp Val Glu Arg Gly Glu Gly Glu Gly
275                 280                 285                 290 atg gcg cga aat cat cac cat ggc cct ggt tta ggt gag gtt ggt gcg        969
Met Ala Arg Asn His His His Gly Pro Gly Leu Gly Glu Val Gly Ala
                    295                 300                 305 ggc tgg atg gat gat gct ggt ggt gag gat aca ggc tac gcc agt ttc       1017
Gly Trp Met Asp Asp Ala Gly Gly Glu Asp Thr Gly Tyr Ala Ser Phe
            310                 315                 320 taa agaagaggag gaacagcaaa gctgcccacg ctcgacagaa gtcggacagt            1070
* cgatattgat acgtccatcc cttttcccct ccctcattt ccacgttcag tctatttcac      1130
attgtgtgca ttttgggttg caagcatggt gttttggtgc ataatggtaa gacaaagggt    1190
aatgaaattg gcaactcttt tggcatgcat cggcgcagca ttttatgggc ggtcagaacc    1250
tctgcgttgt ggcttttagt ttttgaaatt tgcggaatct ggggtgttct tgaggcggat    1310
tctttgtata ttatcataaa gagtagggta gcgctagctc attaatacaa cactttgaat    1370
gtcgtcaaaa aaaaaaaaaa aaaaaaaaaa aaaaaaaaaa aaaaaaaaaa aaaaaaaaaa    1430
aaaaaaaaaa aaaaaaaa                                                  1448
```

<210> SEQ ID NO 23
<211> LENGTH: 322
<212> TYPE: PRT
<213> ORGANISM: Parthenium argentatum
<400> SEQUENCE: 23

```
Met Leu Pro Ala Pro Ala Val Pro Asn Gly Thr Gly Ala Pro Leu Lys
1               5                   10                  15

Asp Glu Pro Ser Asn Pro Asp Gln Ala Gln His Gln Pro Asp Glu Arg
            20                  25                  30

Val Gln His Phe Ile Leu Leu Glu Asp Leu Thr Ala Gly Met Thr Arg
        35                  40                  45

Pro Cys Val Leu Asp Leu Lys Met Gly Thr Arg Gln Tyr Gly Val Glu
    50                  55                  60

Ala Asp Glu Lys Lys Gln Arg Ser Gln Arg Lys Cys Gln Met Thr
65                  70                  75                  80

Thr Ser Ala Gln Leu Gly Val Arg Val Cys Gly Met Gln Ile Trp Asn
                85                  90                  95

Ala Lys Thr Gln Ser Tyr Ile Phe Glu Asp Lys Tyr Phe Gly Arg Asp
            100                 105                 110

Leu Lys Ala Gly Lys Glu Phe Gln Asp Ala Leu Lys Arg Phe Phe Trp
        115                 120                 125

Asp Gly Thr Ser Tyr Lys Ala Ala Asn Arg His Ile Pro Val Ile Leu
    130                 135                 140

Glu Lys Ile Ser Gln Leu Glu Arg Met Ile Arg Lys Leu Pro Gly Tyr
145                 150                 155                 160

Arg Phe Tyr Ala Ser Leu Leu Met Leu Tyr Asp Arg Gly Asp Gly
                165                 170                 175

Glu Ser Lys Glu Lys Asp Ala Ala Pro Ser Leu Pro Asn Gly Leu Ser
            180                 185                 190

Asn Pro Ser Asn Glu Asp Val Ser Thr Ile Pro Ser Gly Leu Thr Ser
        195                 200                 205

Pro Gly Pro Thr Val Ala Ser Lys Pro Ser Pro Lys Lys His Gly Glu
    210                 215                 220

Ile Lys Leu Lys Ile Val Asp Phe Ala Asn Cys Val Thr Ala Glu Asp
```

```
                225                 230                 235                 240
Pro Leu Pro Asp Asp Leu Pro Cys Pro Pro Glu Asn Pro Asp Gly Ile
                    245                 250                 255

Asp Arg Gly Tyr Leu Arg Gly Leu Arg Ser Leu Arg Leu Tyr Phe Gln
            260                 265                 270

Arg Ile Trp Asn Asp Ile Asn Glu Glu Trp Val Glu Arg Gly Glu Gly
        275                 280                 285

Glu Gly Met Ala Arg Asn His His Gly Pro Gly Leu Gly Glu Val
    290                 295                 300

Gly Ala Gly Trp Met Asp Asp Ala Gly Gly Glu Asp Thr Gly Tyr Ala
305                 310                 315                 320

Ser Phe

<210> SEQ ID NO 24
<211> LENGTH: 2270
<212> TYPE: DNA
<213> ORGANISM: Zea mays
<220> FEATURE:
<221> NAME/KEY: CDS
<222> LOCATION: (3)...(953)

<400> SEQUENCE: 24 cc acg cgt ccg cga aaa ttg aga aac att gtt cag tgg acg ccg ttc        47
   Thr Arg Pro Arg Lys Leu Arg Asn Ile Val Gln Trp Thr Pro Phe
     1               5                  10                  15 ttt caa act tac aaa aaa cag agg tat cca tgg gta cag cta gcc gga       95
Phe Gln Thr Tyr Lys Lys Gln Arg Tyr Pro Trp Val Gln Leu Ala Gly
                 20                  25                  30 cac caa ggc aat ttc aaa gcc ggt ccg gaa cct ggt acg atc ctc aag      143
His Gln Gly Asn Phe Lys Ala Gly Pro Glu Pro Gly Thr Ile Leu Lys
             35                  40                  45 aaa ctt tgt ccc aaa gaa cag ttg tgc ttc caa gtg ctg atg aag gac      191
Lys Leu Cys Pro Lys Glu Gln Leu Cys Phe Gln Val Leu Met Lys Asp
         50                  55                  60 gtt ctg aga ccg tac gtg ccc gaa tac aag ggc cac ttg act acc gac      239
Val Leu Arg Pro Tyr Val Pro Glu Tyr Lys Gly His Leu Thr Thr Asp
     65                  70                  75 gac gga gac cta tat ctt cag cta gaa gac ttg ttg ggt gac ttc act      287
Asp Gly Asp Leu Tyr Leu Gln Leu Glu Asp Leu Leu Gly Asp Phe Thr
 80                  85                  90                  95 tcg ccg tgc gtc atg gac tgc aag atc ggc gtc agg acg tat ctg gaa      335
Ser Pro Cys Val Met Asp Cys Lys Ile Gly Val Arg Thr Tyr Leu Glu
                100                 105                 110 gag gaa ctg gcg aaa gcc aaa gag aaa ccc aag ttg aga aaa gac atg      383
Glu Glu Leu Ala Lys Ala Lys Glu Lys Pro Lys Leu Arg Lys Asp Met
            115                 120                 125 tac gaa aaa atg att cag ata gac ccc aac gca cca tcg gag gag gaa      431
Tyr Glu Lys Met Ile Gln Ile Asp Pro Asn Ala Pro Ser Glu Glu Glu
        130                 135                 140 cac cga ctg aag ggt gtg aca aaa ccg agg tac atg gtt tgg agg gag      479
His Arg Leu Lys Gly Val Thr Lys Pro Arg Tyr Met Val Trp Arg Glu
    145                 150                 155 acg att tcg tcc acg gcc acg ttg ggc ttc cgg atc gag ggg atc aag      527
Thr Ile Ser Ser Thr Ala Thr Leu Gly Phe Arg Ile Glu Gly Ile Lys
160                 165                 170                 175 aaa agc gat gga aaa tcg agc aag gac ttc aag acg aca aag aac cgg      575
Lys Ser Asp Gly Lys Ser Ser Lys Asp Phe Lys Thr Thr Lys Asn Arg
                180                 185                 190 gac cag gtg atc gaa gcg ttt cga gat ttc gtc gcc ggt ttc ccg cac      623
Asp Gln Val Ile Glu Ala Phe Arg Asp Phe Val Ala Gly Phe Pro His
```

```
Asp Gln Val Ile Glu Ala Phe Arg Asp Phe Val Ala Gly Phe Pro His
            195                 200                 205 gta atc ccc aag tac ata aac cga ctg aga gcg atc aga gac ata ctg      671
Val Ile Pro Lys Tyr Ile Asn Arg Leu Arg Ala Ile Arg Asp Ile Leu
        210                 215                 220 gtg aac tcc aag ttt ttc act acg cac gag gtg atc ggc agc tcg ctg      719
Val Asn Ser Lys Phe Phe Thr Thr His Glu Val Ile Gly Ser Ser Leu
    225                 230                 235 ctg ttc gtg cac gac agc aag aac gcc aac ata tgg ctt atc gac ttc      767
Leu Phe Val His Asp Ser Lys Asn Ala Asn Ile Trp Leu Ile Asp Phe
240                 245                 250                 255 gca aag acg ctc ata ctt ccg ccg gac atc cgg atc aac cac acg tcc      815
Ala Lys Thr Leu Ile Leu Pro Pro Asp Ile Arg Ile Asn His Thr Ser
                260                 265                 270 gag tgg gtg gtg ggc aac cac gag gac ggt tac ctg atc ggt atc aac      863
Glu Trp Val Val Gly Asn His Glu Asp Gly Tyr Leu Ile Gly Ile Asn
            275                 280                 285 aac ctg ctg gac ata ttc acc gat atg aac gcc gcc acc gcg ttt ccc      911
Asn Leu Leu Asp Ile Phe Thr Asp Met Asn Ala Ala Thr Ala Phe Pro
        290                 295                 300 gtc acg ctc atc gaa gtc acg gcc ccg tcc gaa gtc acc tga              953
Val Thr Leu Ile Glu Val Thr Ala Pro Ser Glu Val Thr  *
    305                 310                 315 acgccgtcga tccccgccgg taccctgact cgctcggcga cccactcgcc ggtgtcattc    1013
gattccagcc acccactcag tggtcttgcg aatcacgtga cccacccgt tgacaatgtg     1073 tgataataat aaatgtctg gcgcaaaata ttccaaaaag tctttttaa attacactt       1133 cgattttcga cgacaaacaa aatgacgacg ttttccgtac ctacctactg tagggttcgt    1193
tccgattgca atcataattt attttacccc cacccaaccc ccgaaccgtt tatggcccac    1253
cagaggattt gccatcagta ttaaaacaat gatctattat agatgttaaa aaataaatat    1313
tatataatta tacatcatcg cggtgtgttg tgtaatatgc ctattataat atgtactata    1373
ttatacacat agcatattat aaaaatagta tattattata ttatattata ataatattat    1433
ggttatgtgt gtttgtgtgg aaatccaata atataaaata atagtattta ttttttaaata   1493 cttgtacgat aatgggacta ctacgtgtga ttctcaaatg atatatat attaatattt      1553 taaacgtaca tttttaattc caaacgtata tgacgtgtgt atatattatt atgatataat    1613
aattactata ctgtgcgtgc gataacataa taattttgta cctaatacat caatcaatta    1673
tccactgcag tgtcgtgtgg ttttatttc gttgttttat tttatcgcta tcactaaatt     1733 actatttta ttattattat tttttttttt tttcaaaaac tttgttttat aatcagctcc     1793
ctccactacc cttttcacaa cccctcttgt ccatgtatta agcaaataat tattttttta    1853
aatacctatc cacgttacaa cgacaataat aataacaata atagtaccta tactttattt    1913
ttatttcctc acgaaaacga gaagtcctca tttctttctc ccgttacagt gtgtgtgtgt    1973
gtgtgtgtgt gtgtgtgtgt gtgtgtgtgt gcgtatgtgt atgtgtgaaa tttttgattt    2033
aattatatat tattataatt ttttctcctt atatttttat ttattattat aacatttttt    2093
ttgtgtgtac agaatattta aataagactt gtaaagaaa cccttgttat attatttat     2153 tttttatttc acttcgcaca tgtgtacata ataaatcgtt atcgccttaa aaaaaaaaa    2213 aaaaaaaaa aaaaaaaaa aaaaaaaaa aaaaaaaaa aaaaaaaaa aaaaaaa           2270

<210> SEQ ID NO 25
<211> LENGTH: 316
<212> TYPE: PRT
```

<213> ORGANISM: Zea mays

<400> SEQUENCE: 25

Thr Arg Pro Arg Lys Leu Arg Asn Ile Val Gln Trp Thr Pro Phe Phe
1               5                   10                  15
Gln Thr Tyr Lys Lys Gln Arg Tyr Pro Trp Val Gln Leu Ala Gly His
            20                  25                  30
Gln Gly Asn Phe Lys Ala Gly Pro Glu Pro Gly Thr Ile Leu Lys Lys
        35                  40                  45
Leu Cys Pro Lys Glu Gln Leu Cys Phe Gln Val Leu Met Lys Asp Val
    50                  55                  60
Leu Arg Pro Tyr Val Pro Glu Tyr Lys Gly His Leu Thr Thr Asp Asp
65                  70                  75                  80
Gly Asp Leu Tyr Leu Gln Leu Glu Asp Leu Gly Asp Phe Thr Ser
                85                  90                  95
Pro Cys Val Met Asp Cys Lys Ile Gly Val Arg Thr Tyr Leu Glu Glu
            100                 105                 110
Glu Leu Ala Lys Ala Lys Glu Lys Pro Lys Leu Arg Lys Asp Met Tyr
        115                 120                 125
Glu Lys Met Ile Gln Ile Asp Pro Asn Ala Pro Ser Glu Glu Glu His
    130                 135                 140
Arg Leu Lys Gly Val Thr Lys Pro Arg Tyr Met Val Trp Arg Glu Thr
145                 150                 155                 160
Ile Ser Ser Thr Ala Thr Leu Gly Phe Arg Ile Glu Gly Ile Lys Lys
                165                 170                 175
Ser Asp Gly Lys Ser Ser Lys Asp Phe Lys Thr Thr Lys Asn Arg Asp
            180                 185                 190
Gln Val Ile Glu Ala Phe Arg Asp Phe Val Ala Gly Phe Pro His Val
        195                 200                 205
Ile Pro Lys Tyr Ile Asn Arg Leu Arg Ala Ile Arg Asp Ile Leu Val
    210                 215                 220
Asn Ser Lys Phe Phe Thr Thr His Glu Val Ile Gly Ser Ser Leu Leu
225                 230                 235                 240
Phe Val His Asp Ser Lys Asn Ala Asn Ile Trp Leu Ile Asp Phe Ala
                245                 250                 255
Lys Thr Leu Ile Leu Pro Pro Asp Ile Arg Ile Asn His Thr Ser Glu
            260                 265                 270
Trp Val Val Gly Asn His Glu Asp Gly Tyr Leu Ile Gly Ile Asn Asn
        275                 280                 285
Leu Leu Asp Ile Phe Thr Asp Met Asn Ala Ala Thr Ala Phe Pro Val
    290                 295                 300
Thr Leu Ile Glu Val Thr Ala Pro Ser Glu Val Thr
305                 310                 315

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
accgcttcca ccatcgccac tcgtc                                      25

<210> SEQ ID NO 27
<211> LENGTH: 30

```
<212> TYPE: DNA
<213> ORGANISM: Artificial Sequence
<220> FEATURE:
<223> OTHER INFORMATION: Primer

<400> SEQUENCE: 27
ccttagacgc agcctttggg tccttcttaa                                     30

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
tcgacccacg cgtccgaaaa aaaaaaaaaa aaaaaa                              36

<210> SEQ ID NO 29
<211> LENGTH: 21
<212> TYPE: PRT
<213> ORGANISM: Artificial Sequence
<220> FEATURE:
<223> OTHER INFORMATION: Consensus Sequence

<400> SEQUENCE: 29

Ile Leu Leu Glu Asn Leu Thr Ser Arg Tyr Glu Val Pro Cys Val Leu
 1               5                  10                  15

Asp Leu Lys Met Gly
            20

<210> SEQ ID NO 30
<211> LENGTH: 33
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(33)
<223> OTHER INFORMATION: Xaa = any amino acid

<400> SEQUENCE: 30

Leu Lys Xaa Pro Glu His Gln Val Ala Gly His Xaa Ala Xaa Xaa Gly
 1               5                  10                  15

Lys Xaa Gly Pro Leu Val Asp Asp Xaa Gly Xaa Phe Tyr Lys Pro Leu
            20                  25                  30

Gln

<210> SEQ ID NO 31
<211> LENGTH: 33
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(33)
<223> OTHER INFORMATION: Xaa = any amino acid

<400> SEQUENCE: 31

Leu Lys Xaa Pro Glu His Gln Val Ala Gly His Xaa Ala Xaa Xaa Gly
 1               5                  10                  15

Lys Xaa Gly Pro Leu Ile Asp Asp Xaa Gly Xaa Phe Tyr Lys Pro Leu
            20                  25                  30
```

Gln

```
<210> SEQ ID NO 32
<211> LENGTH: 33
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(33)
<223> OTHER INFORMATION: Xaa = any amino acid

<400> SEQUENCE: 32

Leu Lys Xaa Pro Asp His Gln Val Ala Gly His Xaa Ala Xaa Xaa Gly
 1               5                  10                  15

Lys Xaa Gly Pro Leu Val Asp Asp Xaa Gly Xaa Phe Tyr Lys Pro Leu
            20                  25                  30
```

Gln

```
<210> SEQ ID NO 33
<211> LENGTH: 33
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(33)
<223> OTHER INFORMATION: Xaa = any amino acid

<400> SEQUENCE: 33

Leu Lys Xaa Pro Asp His Gln Val Ala Gly His Xaa Ala Xaa Xaa Gly
 1               5                  10                  15

Lys Xaa Gly Pro Leu Ile Asp Asp Xaa Gly Xaa Phe Tyr Lys Pro Leu
            20                  25                  30
```

Gln

```
<210> SEQ ID NO 34
<211> LENGTH: 41
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(41)
<223> OTHER INFORMATION: Xaa = any amino acid

<400> SEQUENCE: 34

Val Leu Xaa Asp Leu Xaa Xaa Xaa Xaa Xaa Xaa Pro Ser Val Met Asp
 1               5                  10                  15

Val Lys Xaa Gly Ser Arg Thr Trp Xaa Xaa Xaa Xaa Glu Xaa Tyr
            20                  25                  30

Ile Xaa Lys Cys Leu Xaa Lys Asp Arg
        35                  40

<210> SEQ ID NO 35
<211> LENGTH: 41
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(41)
```

```
<223> OTHER INFORMATION: Xaa = any amino acid

<400> SEQUENCE: 35

Val Leu Xaa Asp Leu Xaa Xaa Xaa Xaa Xaa Xaa Pro Ser Val Met Asp
1               5                   10                  15

Ile Lys Xaa Gly Ser Arg Thr Trp Xaa Xaa Xaa Xaa Glu Xaa Tyr
            20                  25                  30

Ile Xaa Lys Cys Leu Xaa Lys Asp Arg
        35                  40

<210> SEQ ID NO 36
<211> LENGTH: 41
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(41)
<223> OTHER INFORMATION: Xaa = any amino acid

<400> SEQUENCE: 36

Val Leu Xaa Asp Leu Xaa Xaa Xaa Xaa Xaa Xaa Pro Cys Val Met Asp
1               5                   10                  15

Val Lys Xaa Gly Ser Arg Thr Trp Xaa Xaa Xaa Xaa Glu Xaa Tyr
            20                  25                  30

Ile Xaa Lys Cys Leu Xaa Lys Asp Arg
        35                  40

<210> SEQ ID NO 37
<211> LENGTH: 41
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (1)...(41)
<223> OTHER INFORMATION: Xaa = any amino acid

<400> SEQUENCE: 37

Val Leu Xaa Asp Leu Xaa Xaa Xaa Xaa Xaa Xaa Pro Cys Val Met Asp
1               5                   10                  15

Ile Lys Xaa Gly Ser Arg Thr Trp Xaa Xaa Xaa Xaa Glu Xaa Tyr
            20                  25                  30

Ile Xaa Lys Cys Leu Xaa Lys Asp Arg
        35                  40

<210> SEQ ID NO 38
<211> LENGTH: 3851
<212> TYPE: DNA
<213> ORGANISM: Artificial Sequence
<220> FEATURE:
<221> NAME/KEY: terminator
<222> LOCATION: (4)...(1004)
<223> OTHER INFORMATION: glb1 terminator
<220> FEATURE:
<221> NAME/KEY: 3'UTR
<222> LOCATION: (1028)...(1375)
<223> OTHER INFORMATION: 3' UTR of SEQ ID NO:1 (ZM IPPK) complementary
      strand
<220> FEATURE:
<221> NAME/KEY: CDS
<222> LOCATION: (1376)...(2098)
<223> OTHER INFORMATION: coding region of SEQ ID NO:1 (ZM IPPK)
      complementary strand
<220> FEATURE:
```

```
<221> NAME/KEY: 5'UTR
<222> LOCATION: (2099)...(2207)
<223> OTHER INFORMATION: 5' UTR of SEQ ID NO:1 complementary strand
<221> NAME/KEY: promoter
<222> LOCATION: (2195)...(3695)
<223> OTHER INFORMATION: glb1 promoter in 3' to 5' orientation
<220> FEATURE:
<223> OTHER INFORMATION: PHP 17571

<400> SEQUENCE: 38
```

| | | | | | |
|---|---|---|---|---|---|
| aattctttta | tgaataataa | taatgcatat | ctgtgcatta | ctacctggga | tacaagggct | 60 |
| tctccgccat | aacaaattga | gttgcgatgc | tgagaacgaa | cggggaagaa | agtaagcgcc | 120 |
| gcccaaaaaa | aacgaacatg | tacgtcggct | atagcaggtg | aaagttcgtg | cgccaatgaa | 180 |
| aagggaacga | tatgcgttgg | gtagttggga | tacttaaatt | tggagagttt | gttgcataca | 240 |
| ctaatccact | aaagttgtct | atcttttaa | cagctctagg | caggatataa | gatttatatc | 300 |
| taatctgttg | gagttgcttt | tagagtaact | tttctctctg | tttcgtttat | agccgattag | 360 |
| cacaaaatta | aactaggtga | cgagaaataa | agaaaaacgg | aggcagtaaa | aaatacccaa | 420 |
| aaaaatactt | ggagattttt | gtctcaaaat | tatcttctaa | ttttaaaagc | tacatattaa | 480 |
| aaatactata | tattaaaaat | acttcgagat | cattgcttgg | gatgggcagg | gccaatagct | 540 |
| aattgctaag | gatgggctat | atttatgtat | cgtctgaaac | atgtaggggc | taatagttag | 600 |
| atgactaatt | tgctgtgttc | gtacggggtg | ctgtttgagc | ctagcgatga | agggtcatag | 660 |
| tttcatacaa | gaactcactt | ttggttcgtc | tgctgtgtct | gttctcagcg | taacggcatc | 720 |
| aatggatgcc | aaactccgca | aggggacaaa | tgaagaagcg | aagagattat | agaacacgca | 780 |
| cgtgtcatta | tttatttatg | gacttgcctc | agtagcttac | agcatcgtac | ccgcacgtac | 840 |
| atactacaga | gccacactta | ttgcactgcc | tgccgcttac | gtacatagtt | aacacgcaga | 900 |
| gaggtatata | catacacgtc | caacgtctcc | actcaggctc | atgctacgta | cgcacgtcgg | 960 |
| tcgcgcgcca | ccctctcgtt | gcttcctgct | cgttttggcg | aggacagatc | tccatggatc | 1020 |
| cgatctgtct | ttatcactct | cgtcttcaga | agattcatcc | tcagatccaa | tgttttctga | 1080 |
| tactttggga | gccttctttt | cttcaacttt | tgttggctca | tcatccgaac | tttcctcact | 1140 |
| actgtcatct | tcatcctcac | tgctgctttc | ttttttgca | gctgaaagtg | cttcctttgt | 1200 |
| tatcaaatca | aaaatgtcag | gatcctctct | taagaaggac | ccaaaggctg | cgtctaagga | 1260 |
| gtctctggaa | caatgtcaga | aacgaacttg | atcagctagc | agagctcgcc | caggaagttg | 1320 |
| tggtcaatca | ccccatcacc | ctcggccaca | tgggcaaagt | ccaccagctt | cactgttacc | 1380 |
| ccaccccac | ctccgcctgc | tgcgactgca | gcagcatcat | agcccagaag | aatcgacgcc | 1440 |
| gagtagaagt | ggaacagagt | ctgctcctcc | aaccatgcct | tgagctcgcg | cagctgtgac | 1500 |
| aagactccac | cttttcctcc | gtacaccgcc | gccgcgagcg | cgcagtccat | cccctcgtcg | 1560 |
| gcaagcggat | gacacgtagc | gccggagcac | gcggcggacg | ccgacggtgt | ccatagcctt | 1620 |
| cacctccggg | cgctccgtcc | gccacacggc | gccctcgggg | ccgacgactc | ggacgcaaga | 1680 |
| cgcggaatcc | gagcagaacg | ctcgtggtcc | cgcggtcctt | ggcgaggtac | ttggcgatgt | 1740 |
| agggctccgg | cgaactcggt | ggccacgtga | tggcgccgat | cttgatgtct | gcgacgcagg | 1800 |
| gcgcctcaaa | ccccgcgagg | aggtcgtcga | ggacgaggtg | cggatgcggc | tccccgggct | 1860 |
| gcgcctcggt | ggggaggagt | cgcgtgccgt | ggaaccgggg | gaagaaggtg | tctcggatgc | 1920 |
| gggccgggac | ggcggcgtgg | gcggagaacg | cctcatagaa | ggcgacctcg | tgctccccac | 1980 |
| ggtcgccggc | ctggagcggc | ttgtagaaga | ggccggagcc | gtcgatgagc | gggcccagct | 2040 |

```
tgctggcgga ggcgcggtga ccggcgactt ggtgctccgg cgggtggagg tcgggcatgg    2100 tatgggact  atgggagcaa ggggtgacga gtggcgatgg tggaagcggt gggtttgcag    2160
cgcagcggag aaagagattt tcggacgcgt gggtcgactg tgatatcctc gggtgtgtgt    2220
tggatccttg ggttggctgt atgcagaact aaagcggagg tggcgcgcat ttataccagc    2280
gccgggccct ggtacgtggc gcggccgcgc ggctacgtgg aggaaggctg cgtggcagca    2340
gacacacggg tcgccacgtc ccgccgtact ctccttaccg tgcttatccg ggctccggct    2400
cggtgcacgc cagggtgtgg ccgcctctga gcagactttg tcgtgttcca cagtggtgtc    2460
gtgttccggg gactccgatc cgcggcgagc gaccgagcgt gtaaaagagt tcctactagg    2520
tacgttcatt gtatctggac gacgggcagc ggacaatttg ctgtaagaga ggggcagttt    2580
ttttttagaa aaacagagaa ttccgttgag ctaattgtaa ttcaacaaat aagctattag    2640
ttggttttag cttagattaa agaagctaac gactaatagc taataattag ttggtctatt    2700
agttgactca ttttaaggcc ctgtttcaat ctcgcgagat aaactttagc agctattttt    2760
tagctacttt tagccatttg taatctaaac aggagagcta atggtggtaa ttgaaactaa    2820
actttagcac ttcaattcat atagctaaag tttagcagga agctaaactt tatcccgtga    2880
gattgaaacg gggcctaaat ctctcagcta tttttgatgc aaattactgt cactactgga    2940
atcgagcgct ttgccgagtg tcaaagcctg aaaaacactc cgtaaagact ttgcctagtg    3000
tgacactcga caaagagatc tcgacgaaca gtacatcgac aacggcttct ttgtcgagta    3060 cttttttatcg gacacttgac aaagtctttg tcgagtgaac tacattgaaa ctctatgatt    3120
ttatgtgtag gtcacttagg tttctacaca tagtacgtca caactttacc gaaacattat    3180 caaatttta tcacaacctc tatatatgat atcatgacat gtggacaagt ttcattaatt    3240 tctgactta tttgtgtttt atacaatttt taaacaacta gataacaagt tcacggtcat    3300
gtttagtgag catggtgctt gaagattctg gtctgcttct gaaatcggtc gtaacttgtg    3360
ctagataaca tgcatatcat ttattttgca tgcacggttt tccatgtttc gagtgacttg    3420
cagtttaaat gtgaattttc cgaagaaatt caaataaacg aactaaatct aatatttata    3480
gaaaacattt ttgtaaatat gtaattgtgc caaaatggta catgtagatc tacatagtgt    3540
aggaacatac cacaaaaagt ttggttggca aaataaaaaa aataaaatat actttatcga    3600
gtgtccaagg atggcactcg gcaagcttcg gtccgggtca cctttgtcca ccaagatgga    3660
actgcggccg ctcattaatt aagtcaggcg cgcctctagt tgaagacacg ttcatgtctt    3720
catcgtaaga agacactcag tagtcttcgg ccagaatggc ccggaccgaa gcttctgcag    3780
gaattctgag ctagcgaagt tcctattccg aagttcctat tcttcaaaaa gtataggaac    3840
ttcagacgtc c                                                        3851
```

<210> SEQ ID NO 39
<211> LENGTH: 4097
<212> TYPE: DNA
<213> ORGANISM: Artificial Sequence
<220> FEATURE:
<221> NAME/KEY: promoter
<222> LOCATION: (253)...(1127)
<223> OTHER INFORMATION: oleosin promoter
<220> FEATURE:
<221> NAME/KEY: 5'UTR
<222> LOCATION: (1147)...(1228)
<223> OTHER INFORMATION: maize ubiquitin 5' UTR
<220> FEATURE:
<221> NAME/KEY: intron
<222> LOCATION: (1229)...(2231)
<223> OTHER INFORMATION: maize ubiquitin intron

```
<220> FEATURE:
<221> NAME/KEY: 5'UTR
<222> LOCATION: (2257)...(2365)
<223> OTHER INFORMATION: 5' UTR from SEQ ID NO:1 (ZM IPPK)
<220> FEATURE:
<221> NAME/KEY: CDS
<222> LOCATION: (2348)...(3070)
<223> OTHER INFORMATION: coding region from SEQ ID NO:1
<220> FEATURE:
<221> NAME/KEY: 3'UTR
<222> LOCATION: (3071)...(3418)
<223> OTHER INFORMATION: 3' UTR from SEQ ID NO:1
<221> NAME/KEY: terminator
<222> LOCATION: (3463)...(3754)
<223> OTHER INFORMATION: Nos terminator
<220> FEATURE:
<223> OTHER INFORMATION: PHP 17625

<400> SEQUENCE: 39
aacactgata gtttaaactg aaggcgggaa acgacaatct gatcatgagc ggagaattaa     60
gggagtcacg ttatgacccc cgccgatgac gcgggacaag ccgttttacg tttggaactg    120
acagaaccgc aacgttgaag gagccactca gcccaagctg gtacgattgt aatacgactc    180
actatagggc gaattgagcg ctgtttaaac gctcttcaac tggaagagcg gttacccgga    240
ccggaattcg aggatccgat tgactatctc attcctccaa acccaaacac ctcaaatata    300
tctgctatcg ggattggcat tcctgtatcc ctacgcccgt gtaccccctg tttagagaac    360
ctcccaaggt ataagatggc gaagattatt gttgtcttgt cttccatcat atatcgagtc    420
tttccctagg atattattat tggcaatgag cattacacgg ttaatcgatt gagagaacat    480
gcatctcacc ttcagcaaat aattacgata atccatattt tacgcttcgt aacttctcat    540
gagtttcgat atacaaattt gttttctgga caccctacca ttcatcctct tcggagaaga    600
gaggaagtgt cctcaattta aatatgttgt catgctgtag ttcttcaccc aatctcaaca    660
ggtaccaagc acattgtttc cacaaattat attttagtca caataaatct atattattat    720
taatatacta aaactatact gacgctcaga tgcttttact agttcttgct agtatgtgat    780
gtaggtctac gtggaccaga aaatagtgag acacggaaga caaagaagt aaaagaggcc    840 cggactacgg cccacatgag attcggcccc gccacctccg gcaaccagcg gccgatccaa    900
cggaagtgcg cgcacacaca caacctcgta tatatcgccg cgcggaagcg gcgcgaccga    960
ggaagccttg tcctcgacac cccctacaca ggtgtcgcgc tgcccccgac acgagtcccg   1020
catgcgtccc acgcggccgc gccagatccc gcctccgcgc gttgccacgc cctctataaa   1080
cacccagctc tccctcgccc tcatctacct cactcgtagt cgtagctcga aattcgatgg   1140
gtcgactccc caacctcgtg ttgttcggag cgcacacaca cacaaccaga tctcccccaa   1200
atccacccgt cggcacctcc gcttcaaggt acgccgctcg tcctcccccc ccccctctc    1260 taccttctct agatcggcgt tccggtccat gcatggttag ggcccggtag ttctacttct   1320
gttcatgttt gtgttagatc cgtgtttgtg ttagatccgt gctgctagcg ttcgtacacg   1380
gatgcgacct gtacgtcaga cacgttctga ttgctaactt gccagtgttt ctctttgggg   1440
aatcctggga tggctctagc cgttccgcag acgggatcga tttcatgatt ttttttgttt   1500
cgttgcatag ggtttggttt gcccttttcc tttatttcaa tatatgccgt gcacttgttt   1560
gtcgggtcat cttttcatgc ttttttttgt cttggttgtg atgatgtggt ctggttgggc   1620
ggtcgttcta gatcggagta gaattctgtt tcaaactacc tggtggatt attaattttg    1680 gatctgtatt tgtgtgccat acatattcat agttacgaat tgaagatgat ggatggaaat   1740
atcgatctag gataggtata catgttgatg cgggttttac tgatgcatat acagagatgc   1800
```

```
tttttgttcg cttggttgtg atgatgtggt gtggttgggc ggtcgttcat tcgttctaga   1860
tcggagtaga atactgtttc aaactacctg gtgtatttat taattttgga actgtatgtg   1920
tgtgtcatac atcttcatag ttacgagttt aagatggatg gaaatatcga tctaggatag   1980
gtatacatgt tgatgtgggt tttactgatg catatacatg atggcatatg cagcatctat   2040
tcatatgctc taaccttgag tacctatcta ttataataaa caagtatgtt ttataattat   2100
tttgatcttg atatacttgg atgatggcat atgcagcagc tatatgtgga ttttttttagc   2160 cctgccttca tacgctattt atttgcttgg tactgtttct tttgtcgatg ctcaccctgt   2220
tgtttggtgt tacttctgca ggtcgactct agaccccgcg tccgaaaatc tctttctccg   2280
ctgcgctgca aacccaccgc ttccaccatc gccactcgtc accccttgct cccatagtcc   2340 ccatacc atg ccc gac ctc cac ccg ccg gag cac caa gtc gcc ggt cac     2389
        Met Pro Asp Leu His Pro Pro Glu His Gln Val Ala Gly His
        1               5                   10
```

```
cgc gcc tcc gcc agc aag ctg ggc ccg ctc atc gac ggc tcc ggc ctc     2437
Arg Ala Ser Ala Ser Lys Leu Gly Pro Leu Ile Asp Gly Ser Gly Leu
15                  20                  25                  30
```

```
ttc tac aag ccg ctc cag gcc ggc gac cgt ggg gag cac gag gtc gcc     2485
Phe Tyr Lys Pro Leu Gln Ala Gly Asp Arg Gly Glu His Glu Val Ala
                35                  40                  45
```

```
ttc tat gag gcg ttc tcc gcc cac gcc gcc gtc ccg gcc cgc atc cga     2533
Phe Tyr Glu Ala Phe Ser Ala His Ala Ala Val Pro Ala Arg Ile Arg
        50                  55                  60
```

```
gac acc ttc ttc ccc cgg ttc cac ggc acg cga ctc ctc ccc acc gag     2581
Asp Thr Phe Phe Pro Arg Phe His Gly Thr Arg Leu Leu Pro Thr Glu
            65                  70                  75
```

```
gcg cag ccc ggg gag ccg cat ccg cac ctc gtc ctc gac gac ctc ctc     2629
Ala Gln Pro Gly Glu Pro His Pro His Leu Val Leu Asp Asp Leu Leu
80                  85                  90
```

```
gcg ggg ttt gag gcg ccc tgc gtc gca gac atc aag atc ggc gcc atc     2677
Ala Gly Phe Glu Ala Pro Cys Val Ala Asp Ile Lys Ile Gly Ala Ile
95                  100                 105                 110
```

```
acg tgg cca ccg agt tcg ccg gag ccc tac atc gcc aag tac ctc gcc     2725
Thr Trp Pro Pro Ser Ser Pro Glu Pro Tyr Ile Ala Lys Tyr Leu Ala
                115                 120                 125
```

```
aag gac cgc ggg acc acg agc gtt ctc ctc gga ttc cgc gtc ttg cgt     2773
Lys Asp Arg Gly Thr Thr Ser Val Leu Leu Gly Phe Arg Val Leu Arg
        130                 135                 140
```

```
ccg agt cgt cgg ccc cga ggg cgc cgt gtg gcg gac gga gcg ccc gga     2821
Pro Ser Arg Arg Pro Arg Gly Arg Arg Val Ala Asp Gly Ala Pro Gly
            145                 150                 155
```

```
ggt gaa ggc tat gga cac cgt cgg cgt ccg ccg cgt gct ccg gcg cta     2869
Gly Glu Gly Tyr Gly His Arg Arg Arg Pro Pro Arg Ala Pro Ala Leu
160                 165                 170
```

```
cgt gtc atc cgc ttg ccg acg agg gga tgg act gcg cgc tcg cgg cgg     2917
Arg Val Ile Arg Leu Pro Thr Arg Gly Trp Thr Ala Arg Ser Arg Arg
175                 180                 185                 190
```

```
cgg tgt acg gag gaa aag gtg gag tct tgt cac agc tgc gcg agc tca     2965
Arg Cys Thr Glu Glu Lys Val Glu Ser Cys His Ser Cys Ala Ser Ser
                195                 200                 205
```

```
agg cat ggt tgg agg agc aga ctc tgt tcc act tct act cgg cgt cga     3013
Arg His Gly Trp Arg Ser Arg Leu Cys Ser Thr Ser Thr Arg Arg Arg
        210                 215                 220
```

```
ttc ttc tgg gct atg atg ctg ctg cag tcg cag cag gcg gag gtg ggg     3061
Phe Phe Trp Ala Met Met Leu Leu Gln Ser Gln Gln Ala Glu Val Gly
            225                 230                 235
```

```
gtg ggg taa cagtgaagct ggtggactt  gcccatgtgg ccgagggtga           3110
Val Gly *
    240 tggggtgatt gaccacaact tcctgggcga gctctgctag ctgatcaagt tcgtttctga  3170 cattgttcca gagactcctt agacgcagcc tttgggtcct tcttaagaga ggatcctgac  3230 atttttgatt tgataacaaa ggaagcactt tcagctgcaa aaaaagaaag cagcagtgag  3290 gatgaagatg acagtagtga ggaaagttcg gatgatgagc caacaaaagt tgaagaaaag  3350 aaggctccaa aagtatcaga aaacattgga tctgaggatg aatcttctga agacgagagt  3410 gataaagaca gatcggatcc atggagatct gtcgactcta gacccggggt acctaaagaa  3470 ggagtgcgtc gaagcagatc gttcaaacat ttggcaataa agtttcttaa gattgaatcc  3530 tgttgccggt cttgcgatga ttatcatata atttctgttg aattacgtta agcatgtaat  3590 aattaacatg taatgcatga cgttatttat gagatgggtt tttatgatta gagtcccgca  3650 attatacatt taatacgcga tagaaaacaa aatatagcgc gcaaactagg ataaattatc  3710 gcgcgcggtg tcatctatgt tactagatcg atgtcgaatc gatgggcccc ggccgaagct  3770 tcggtccggg tcacctttgt ccaccaagat ggaactgcgg ccgctcatta attaagtcag  3830 gcgcgcctct agttgaagac acgttcatgt cttcatcgta agaagacact cagtagtctt  3890 cggccagaat ggcccggacc gaagcttctg caggaattct gagctagcga agttcctatt  3950 ccgaagttcc tattcttcaa aaagtatagg aacttcagac gtcctcgagt ccgtcctgta  4010 gaaaccccaa cccgtgaaat caaaaaactc gacggcctgt gggcattcag tctggatcgc  4070 gaaaactgtg gaattgatcc agaattc                                     4097
```

INOSITOL POLYPHOSPHATE KINASE GENES AND USES THEREOF

CROSS-REFERENCE TO RELATED APPLICATIONS

This application is a continuation-in-part of co-pending U.S. application Ser. No. 10/042,894 filed Jan. 9, 2002 which claims the benefit of U.S. Application Ser. No. 60/261,465 filed Jan. 12, 2001, which is herein incorporated by reference.

TECHNICAL FIELD

The present invention relates to the field of animal nutrition. Specifically, the present invention relates to the identification and use of genes encoding enzymes involved in the metabolism of phytate in plants and the use of these genes and mutants thereof to reduce the levels of phytate, and/or increase the levels of non-phytate phosphorus in food or feed.

BACKGROUND OF THE INVENTION

The role of phosphorous in animal nutrition is well recognized, it is a critical component of the skeleton, nucleic acids, cell membranes and some vitamins. Though phosphorous is essential for the health of animals, not all phosphorous in feed is bioavailable.

Phytates are the major form of phosphorous in seeds, for example phytate represents about 60-80% of total phosphorous in corn and soybean. When seed-based diets are fed to non-ruminants, the consumed phytic acid forms salts with several important mineral nutrients, such as potassium, calcium, and iron, and also binds proteins in the intestinal tract. These phytate complexes cannot be metabolized by monogastric animals and are excreted, effectively acting as antinutritional factors by reducing the bioavailability of dietary phosphorous and minerals. Phytate-bound phosphorous in animal excreta also has a negative environmental impact, contributing to surface and ground water pollution.

There have been two major approaches to reducing the negative nutritional and environmental impacts of phytate in seed. The first involves post-harvest interventions, which increase the cost and processing time of feed. Post-harvest processing technologies remove phytic acid by fermentation or by the addition of compounds, such as phytases.

The second is a genetic approach, which has been strongly correlated with undesirable agronomic characteristics. One genetic approach involves developing crop germplasm with heritable reductions in seed phytic acid. Heritable quantitative variation in seed phytic acid has been observed among lines in several crop species, but is also highly and positively correlated with less desirable characteristics. While some variability for phytic acid was observed, there was no change in non-phytate phosphorous, only 2% of the observed variation in phytic acid was heritable whereas 98% of the variation was attributed to environmental factors.

Another traditional genetic approach involves selecting low phytate lines from a mutagenized population to produce germplasm separated from the undesirable correlated traits seen in traditional breeding. Most mutant lines are a loss of function, presumably blocked in the phytic acid biosynthetic pathway; therefore low phytic acid accumulation will likely be a recessive trait. In certain cases, this approach has revealed that homozygosity for substantially reduced phytate proved lethal.

A more modern genetic approach is transgenic technology, which has been used to increase phytase levels in plants. These transgenic plant tissues or seed have been used as dietary supplements, but this approach has not been used to reduce phytic acid accumulation in seed.

The biosynthetic route leading to phytate is complex and not completely understood. Without wishing to be bound by any particular theory of the formation of phytate, it is believed that the synthesis may be mediated by a series of one or more ADP-phosphotransferases, ATP-dependent kinases and isomerases. A number of intermediates have been isolated including, for example, monophosphates such as D-myo-inositol 3-monophosphate, diphosphates (IP2s) such as D-myo-inositol 3,4-bisphosphate, triphosphates (IP3s) such as D-myo-inositol 3,4,6 trisphosphate, tetraphosphates (IP4s) such as D-myo-inositol 3,4,5,6-tetrakisphosphates, and pentaphosphates (IP5s) such as D-myo-inositol 1,3,4,5,6 pentakisphosphate. The phosphorylation of the IP5 to IP6 is found to be reversible. Several futile cycles of dephosphorylation and rephosphorylation of the P5 and P6 forms have been reported as well as a cycle involving glucose-6-phosphate->D-myo-inositol 3-monophosphate->myo-inositol; the last step being completely reversible, indicating that control of metabolic flux through this pathway may be important.

Based on the foregoing, there exists the need to improve the nutritional content of plants, particularly corn and soybean by increasing non-phytate phosphorous and reducing seed phytate. This invention differs from the foregoing approaches in that it provides tools and reagents that allow the skilled artisan, by the application of, inter alia, transgenic methodologies to influence the metabolic flux in respect to the phytic acid pathway.

SUMMARY OF THE INVENTION

Inositol polyphosphate kinases are a class of proteins originally discovered in yeast and identified as part of a signal transduction pathway. These enzymes can use several inositol phosphate species as substrates with adenosine triphosphate (ATP) in a phosphorylation reaction yielding the products adenosine diphosphate (ADP) and phosphorylated inositol phosphate (n+1). This invention foresees using these nucleic acids or polypeptides, or variants thereof, to modulate the flux through the phytic acid biosynthetic pathway in order to improve the nutritional quality of feed, corn and soy in particular, and to reduce the environmental impact of animal waste by creating seed with higher available phosphorous or lower phytate levels.

DETAILED DESCRIPTION OF THE INVENTION

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, the term "nucleic acid" means a polynucleotide and includes single or multi-stranded polymers of deoxyribonucleotide or ribonucleotide bases. Nucleic acids may also include fragments and modified nucleotides. Therefore, as used herein, the terms "nucleic acid" and "polynucleotide" are used interchangably.

As used herein, "inositol polyphosphate kinase polynucleotide" is a nucleic acid of the present invention and means a nucleic acid, or fragment thereof, comprising a polynucleotide encoding a polypeptide with inositol polyphosphate kinase activity or a useful fragment thereof.

As used herein, "IPPK" means inositol polyphosphate kinase in regards to any nucleic acid or polypeptide of the present invention, or the associated functional activity.

As used herein, "polypeptide" means proteins, protein fragments, modified proteins (e.g., glycosylated, phosphorylated, or other modifications), amino acid sequences and synthetic amino acid sequences. The polypeptide can be modified or not. Therefore, as used herein, "polypeptide" and "protein" are used interchangably.

As used herein, "inositol polyphosphate kinase polypeptide" is a polypeptide of the present invention which is capable of phosphorylating an appropriate inositol phosphate substrate and refers to one or more amino acid sequences, in modified or unmodified form. The term is also inclusive of fragments, variants, homologs, alleles or precursors (e.g., preproproteins or proproteins) or activity thereof.

As used herein, "plant" includes plants and plant parts including but not limited to plant cells and plant tissues such as leaves, stems, roots, flowers, pollen, and seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid, functional fragments. Alternatively, fragments of a nucleotide sequence that can be useful as hybridization probes may not encode fragment proteins retaining biological activity. Thus, fragments of a nucleotide sequence are generally greater than 25, 50, 100, 150, 200, 250, 300, 350, 400, 450, 500, 600, or 700 nucleotides and up to and including the entire nucleotide sequence encoding the proteins of the invention. Generally the probes are less than 1000 nucleotides and often less than 500 nucleotides. Fragments of the invention include antisense sequences used to decrease expression of the inventive polynucleotides. Such antisense fragments may vary in length ranging from greater than 25, 50, 100, 200, 300, 400, 500, 600, or 700 nucleotides and up to and including the entire coding sequence.

By "functional equivalent" as applied to a polynucleotide or a protein is intended a polynucleotide or a protein of sufficient length to modulate the level of IPPK protein activity in a plant cell. A polynucleotide functional equivalent can be in sense or antisense orientation.

By "variants" is intended substantially similar sequences. Generally, nucleic acid sequence variants of the invention will have at least 60%, 65%, 70%, 75%, 80%, 85%, 86%, 87%, 88%, 89%, 90%, 91%, 92%, 93%, 94%, 95%, 96%, 97%, 98% or 99% sequence identity to the native nucleotide sequence, wherein the % sequence identity is based on the entire sequence and is determined by GAP 10 analysis using default parameters. Generally, polypeptide sequence variants of the invention will have at least about 60%, 65%, 70%, 75%, 80%, 85%, 90%, 95% or 98% sequence identity to the native protein, wherein the % sequence identity is based on the entire sequence and is determined by GAP 10 analysis using default parameters. GAP uses the algorithm of Needleman and Wunsch (*J. Mol. Biol.* 48:443-453, 1970) to find the alignment of two complete sequences that maximizes the number of matches and minimizes the number of gaps.

As used herein "transformation" includes stable transformation and transient transformation.

As used herein "stable transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimeraplasty or transposon insertion.

As used herein "transient transformation" refers to the transfer of a nucleic acid fragment or protein into the nucleus (or DNA-containing organelle) of a host organism resulting in gene expression without integration and stable inheritance.

"IPPK enzyme-binding molecule", as used herein, refers to molecules or ions which bind or interact specifically with phytate biosynthetic enzyme polypeptides or polynucleotides of the present invention, including, for example enzyme substrates, cofactors, antagonists, inhibitors, cell membrane components and classical receptors. Binding between polypeptides of the invention and such molecules, including binding or interaction molecules may be exclusive to polypeptides of the invention, or it may be highly specific for polypeptides of the invention, or it may be highly specific to a group of proteins that includes polypeptides of the invention, or it may be specific to several groups of proteins at least one of which includes a polypeptide of the invention. Binding molecules also include antibodies and antibody-derived reagents that bind specifically to polypeptides of the invention.

"High phosphorous transgenic", as used herein, means an entity which, as a result of recombinant genetic manipulation, produces seed with a heritable decrease in phytic acid percentage and/or increase in non-phytate phosphorous percentage as compared to a corresponding plant that has not been transformed.

"Phytic acid", as used herein, means myo-inositol tetraphosphoric acid, myo-inositol pentaphosphoric acid or myo-inositol hexaphosphoric acid. As a salt with cations, phytic acid is "phytate".

"Non-phytate phosphorous", as used herein, means total phosphorus minus phytate phosphorous.

"Non-ruminant animal" means an animal with a simple stomach divided into the esophageal, cardia, fundus and pylorus regions. A non-ruminant animal additionally implies a species of animal without a functional rumen. A rumen is a section of the digestive system where feedstuff/food is soaked and subjected to digestion by microorganisms before passing on through the digestive tract. This phenomenon does not occur in a non-ruminant animal. The term non-ruminant animal includes but is not limited to humans, swine, poultry, cats and dogs.

Nucleic Acids

The inositol polyphosphate kinase gene family encodes a class of enzymes capable of using several different inositol phosphates as substrates in a phosphorylation reaction, using adenosine triphosphate (ATP) as the phosphate donor, resulting in the products adenosine diphosphate (ADP) and a phosphorylated inositol phosphate. It is expected that modulating the expression and/or level of the nucleic acids of the present invention will modulate the phytate biosynthetic pathway providing methods to increase available phosphorous, decrease phytate and/or decrease polluting phytate-bound phosphorous in animal waste.

The isolated nucleic acids of the present invention can be made using (a) standard recombinant methods, (b) synthetic techniques, or combinations thereof. In some embodiments, the polynucleotides of the present invention can be cloned, amplified, or otherwise constructed from a monocot or dicot. Typical examples of monocots are corn, sorghum, barley, wheat, millet, rice, or turf grass. Typical dicots include soybeans, safflower, sunflower, canola, alfalfa, potato, or cassava.

Functional fragments included in the invention can be obtained using primers which selectively hybridize under stringent conditions. Primers are generally at least 12 bases in length and can be as high as 200 bases, but will generally be from 15 to 75, or more likely from 15 to 50 bases. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, pages 8.0.3-8.5.9 *Current Protocols in Molecular Biology*, Ausubel et al., Eds., Greene Publishing and Wiley-Interscience, New York (1995). Also, see generally, McPherson (ed.), *DIRECTED MUTAGENESIS: A Practical Approach*, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alter, add or delete a single amino acid or a small percentage of amino acids in the encoded sequence. A "conservatively modified variant" is an alteration which results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al., *Proc. Natl. Acad. Sci. USA* 94:4504-4509 (1997).

The present invention also includes the use of 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387-395 (1984)) or MacVector 4.1 (Eastman Kodak Co., New Haven, Conn.).

For example, the inventive nucleic acids can be optimized for enhanced expression in plants of interest. See, for example, EPA0359472; WO91/16432; Perlak et al. (1991) *Proc. Natl. Acad. Sci. USA* 88:3324-3328; and Murray et al. (1989) *Nucleic Acids Res.* 17:477-498. In this manner, the polynucleotides can be synthesized utilizing plant-preferred codons. See, for example, Murray et al. (1989) *Nucleic Acids Res.* 17:477-498, the disclosure of which is incorporated herein by reference.

The present invention provides subsequences comprising isolated nucleic acids containing at least 20 contiguous bases of the inventive sequences. For example the isolated nucleic acid includes those comprising at least 20, 30, 40, 50, 60, 70, 80, 90, 100, 200, 300, 400, 500, 600, 700 or 800 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexahistidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clontech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics*, 37:327-336 (1996). Other methods for producing full-length libraries are known in the art. See, e.g., Edery et al., *Mol. Cell Biol.* 15(6):3363-3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705-5711 (1990); Patanjali et al., *Proc. Natl. Acad. U.S.A.* 88:1943-1947 (1991); U.S. Pat. Nos. 5,482,685 and 5,637,685; and Soares et al., *Proc. Natl. Acad. Sci. USA* 91:9228-9232 (1994).

Subtracted cDNA libraries are another means to increase the proportion of less abundant cDNA species. See, Foote et al., in *Plant Molecular Biology: A Laboratory Manual*, Clark, Ed., Springer-Verlag, Berlin (1997); Kho and Zarbl, *Technique* 3(2):58-63 (1991); Sive and St. John, *Nucl. Acids Res.* 16(22):10937 (1988); *Current Protocols in Molecular Biology*, Ausubel et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1-3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related polynucleotides directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols: A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. *BioTechniques*, 22(3):481-486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues such as ears, seedlings, leaves, stalks, roots, pollen, or seeds. Good results have been obtained using tissues such as corn nucellus 5 days after silking, corn embryos 20 days after pollination, pooled primary and secondary immature ears from corn, corn leaves at the V3-V4 stage, 20 day old cold germinated corn seedlings, V5 corn roots, soybean 8 day old root tissue, eucalyptus capsules (possibly fertile seed), and Guayule stem bark.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.) and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90-99 (1979); the phosphodiester method of Brown et al., *Meth. EnzymoL* 68:109-151 (1979); the diethylphosphoramidite method of Beaucage et al., *Tetra. Lett.* 22:1859-1862 (1981); the solid phase phosphoramidite triester method described by Beaucage and Caruthers, *Tetra. Letts.* 22(20): 1859-1862 (1981), e.g., using an automated synthesizer, e.g., as described in Needham-VanDevanter et al., *Nucleic Acids Res.* 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The nucleic acids of the present invention include those amplified using the following primer pairs: SEQ ID NOS: 26 and 27.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual*; Cold Spring Harbor, N.Y.; (1989); Gelvin et al.; *Plant Molecular Biology Manual* (1990); *Plant Biotechnology: Commercial Prospects and Problems*, eds. Prakash et al.; Oxford & IBH Publishing Co.; New Delhi, India; (1993); and Heslot et al.; *Molecular Biology and Genetic Engineering of Yeasts*; CRC Press, Inc., USA; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'- promoter derived from T-DNA of *Agrobacterium tumefaciens*, the actin promoter, the ubiquitin promoter, the histone H2B promoter (Nakayama et al., 1992, *FEBS Lett* 30:167-170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the AdhI promoter which is inducible by hypoxia or cold stress, the Hsp70promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, pollen, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, (Boronat, A., et al., *Plant Sci.* 47:95-102 (1986); Reina, M., et al., *Nucleic Acids Res.* 18(21):6426 (1990); Kloesgen, R. B., et al., *Mol. Gen. Genet.* 203:237-244 (1986)), as well as the globulin 1, oleosin and the phaseolin promoters. The disclosures each of these are incorporated herein by reference in their entirety.

The barley or maize Nuc1 promoter, the maize Cim1 promoter or the maize LTP2 promoter can be used to preferentially express in the nucellus. See, for example WO 00/11177, the disclosure of which is incorporated herein by reference.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395-4405 (1988); Callis et al., *Genes Dev.* 1:1183-1200 (1987). Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene encodes antibiotic or herbicide resistance. Suitable genes include those coding for resistance to the antibiotics spectinomycin and streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., *Meth. In Enzymol.* 153:253-277 (1987). Exemplary *A. tumefaciens* vectors useful herein are plasmids pKYLX6 and pKYLX7 of Schardl et al., *Gene* 61:1-11 (1987) and Berger et al., *Proc. Natl. Acad. Sci. USA* 86:8402-8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Natl. Acad. Sci. USA* 85:8805-8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279-289 (1990) and U.S. Pat. No. 5,034,323.

Recent work has shown suppression with the use of double stranded RNA. Such work is described in Tabara et al., *Science* 282:5388:430-431 (1998), WO 99/53050 and WO 98/53083.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585-591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065-4076, describe covalent bonding of a single-stranded DNA fragment with alkylating derivatives of nucleotides complementary to target sequences. A report of similar work by the same group is that by Knorre, D. G., et al., *Biochimie* (1985) 67:785-789. Iverson and Dervan also showed sequence-specific cleavage of single-stranded DNA mediated by incorporation of a modified nucleotide which was capable of activating cleavage (*J. Am. Chem. Soc.* (1987) 109:1241-1243). Meyer, R. B., et al., *J. Am. Chem. Soc.* (1989) 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197-3203. Use of crosslinking in triple-helix forming probes was also disclosed by Home et al., *J. Am. Chem. Soc.* (1990) 112:2435-2437. Use of N4, N4-ethanocytosine as an alkylating agent to crosslink to single-stranded oligonucleotides has also been described by Webb and Matteucci, *J. Am. Chem. Soc.* (1986) 108:2764-2765; *Nucleic Acids Res* (1986) 14:7661-7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672, 593; 5,484,908; 5,256,648; and, 5,681,941.

Gene or Trait Stacking

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of IPPKs (SEQ ID NOS: 1, 3, 5, 7, 9, 11, 13, 15, 20, 22, and 24), or with other genes implicated in phytic acid metabolic pathways such as phytase; Lpa1, Lpa2 (see U.S. Pat. Nos. 5,689,054 and 6,111,168); myo-inositol 1-phosphate synthase (MI1PS), inositol 1,3,4-trisphosphate 5/6 kinases (IT-PKs) and myo-inositol monophophatase (IMP) (see U.S. Provisional Application Ser. No. 60/325,308 filed Sept. 27, 2001, and WO 99/05298) and the like, the disclosures of which are herein incorporated by reference. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232, 529); balanced amino acids (e.g. hordothionins (U.S. Pat. Nos. 5,990,389; 5,885,801; 5,885,802; and 5,703,409); barley high lysine (Williamson et al. (1987) *Eur. J Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. Provisional Application Ser. No. 60/246,455, filed Nov. 11, 2000); and thioredoxins (U.S. Provisional Application Ser. No. 60/250,705, filed Dec. 12, 2000)), the disclosures of which are herein incorporated by reference. The polynucleotides of the present invention can also be stacked with traits desirable for insect, disease or herbicide resistance (e.g. *Bacillus thuringiensis* toxic proteins (U.S. Pat. Nos. 5,366,892; 5,747,450; 5,737,514; 5,723, 756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232, 529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J Bacterol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

Proteins

IPPK proteins are a class of proteins in inositol phosphate metabolism that are all involved in the phosphorylation of their appropriate inositol phosphate substrates, including but not limited to IP2, IP3, IP4, and IP5, using ATP as the phosphate donor. The sequences of the present invention have homology to a conserved inositol phosphate binding motif domain show in SEQ ID NO: 29. Analysis of the polypeptide sequences of the present invention reveals the consensus domains shown in SEQ ID NOS: 30-37. It is expected that modulation of the expression of these proteins of the present invention will provide methods to improve the quality of animal feed by reducing the level of phytate and/or increasing the level of bioavailable phosphorous. Reducing phytate levels should also result in less environment-polluting phosphorous in the waste of non-ruminant animals.

Proteins of the present invention include proteins having the disclosed sequences as well proteins coded by the disclosed polynucleotides. In addition, proteins of the present invention include proteins derived from the native protein by deletion, addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants can generally be made such that variants continue to possess the desired activity.

The isolated proteins of the present invention include a polypeptide comprising at least 25 contiguous amino acids encoded by any one of the nucleic acids of the present invention, or polypeptides that are conservatively modified variants thereof. The proteins of the present invention or variants thereof can comprise any number of contiguous amino acid residues from a polypeptide of the present invention, wherein that number is selected from the group of integers consisting of from 25 to the number of residues in a full-length polypeptide of the present invention. Optionally, this subsequence of contiguous amino acids is at least 25, 30, 40, 50, 60, 70, 80, 90, 100, 150, 200, 250, 300, 350, 400, 450, or 500 amino acids in length.

The present invention includes catalytically active polypeptides (i.e., enzymes). Catalytically active polypeptides will generally have a specific activity of at least about 20%, 30%, 40%, 50%, 60%, 70%, 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least about 30%, 40%, 50%, 60%, 70%, 80%, 90%, or 95% that of the native (non-synthetic), endogenous polypeptide. Methods of assaying and quantifying measures of enzymatic activity and substrate specificity ($k_{cat}/K_m$), are well known to those of skill in the art. See, e.g., Segel, *Biochemical Calculations*, $2^{nd}$ ed., John Wiley and Sons, New York (1976).

The present invention includes modifications that can be made to an inventive protein. In particular, it may be desirable to diminish the activity of the gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in recombinantly engineered cells such as bacteria, yeast, insect, mammalian, or plant cells. The cells produce the protein in a non-natural condition (e.g., in quantity, composition, location, and/or time), because they have been genetically altered through human intervention to do so.

Typically, an intermediate host cell may be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes and eukaryotes. Prokaryotes include bacterial hosts such as *Escherichia coli, Salmonella typhimurium*, and *Serratia marcescens*. Eukaryotic hosts such as yeast, insect cells or filamentous fungi may also be used in this invention.

Commonly used prokaryotic control sequences include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus sp.* and *Salmonella* (Palva et al., *Gene* 22:229-235 (1983); Mosbach et al., *Nature* 302:543-545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The baculovirus expression system (BES) is a eukaryotic, helper-independent expression system which has been used to express hundreds of foreign genes (Luckow, V., Ch. 4 "Cloning and Expression of Heterologous Genes in Insect Cells with Baculovirus Vectors" in *Recombinant DNA Technology and Applications*, A. Prokop et al., Eds. McGraw-Hill, Inc. (1991); Luckow, V., Ch. 10 "Insect Expression Technology" in *Principles & Practice of Protein Engineering*, J. L. Cleland and C. S. Craig, Eds. John Wiley & Sons, (1994)).

Recombinant baculoviruses are generated by inserting the particular gene- or genes-of-interest into the baculovirus genome using established protocols with vectors and reagents from commercial suppliers (e.g., Invitrogen, Life Technologies Incorporated). Commercial vectors are readily available with various promoters, such as polyhedrin and p10, optional signal sequences for protein secretion, or affinity tags, such as 6× histidine. These recombinant viruses are grown, maintained and propagated in commercially available cell lines derived from several insect species including *Spodoptera frugiperda* and *Trichoplusia ni*. The insect cells can be cultured using well-established protocols in a variety of different media, for example, with and without bovine serum supplementation. The cultured cells are infected with the recombinant viruses and the gene-of-interest polypeptide is expressed. Proteins expressed with the baculovirus system have been extensively characterized and, in many cases, their post-translational modifications such as phosphorylation, acylation, etc., are identical to the natively expressed protein.

A protein of the present invention, once expressed, can be isolated from cells by lysing the cells and applying standard protein isolation techniques to the lysates. The monitoring of the purification process can be accomplished by using Western blot techniques or radioimmunoassay or other standard immunoassay techniques. Expression cassettes are also available which direct the expressed protein to be secreted from the cell into the media. In these cases, the expressed protein can be purified from the cell growth media using standard protein purification techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology*. Vol. 2: *Special Methods in Peptide Synthesis, Part A.*; Merrifield et al., *J. Am. Chem. Soc.* 85:2149-2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide)) are known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant.

The method comprises transforming a plant cell with an expression cassette comprising a polynucleotide of the present invention to obtain a transformed plant cell, growing the transformed plant cell under conditions allowing expression of the polynucleotide in the plant cell in an amount sufficient to modulate concentration and/or composition in the plant cell.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565, 350; Zarling et al., PCT/US93/03868. One method of down-regulation of the protein involves using PEST sequences that provide a target for degradation of the protein.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, content of the polypeptide is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In certain embodiments, the polypeptides of the present invention are modulated in monocots or dicots, for example maize, soybeans, sunflower, safflower, sorghum, canola, wheat, alfalfa, rice, barley and millet.

Means of detecting the proteins of the present invention are not critical aspects of the present invention. The proteins can be detected and/or quantified using any of a number of well-recognized immunological binding assays (see, e.g., U.S. Pat Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, New York (1991); and Non-isotopic Immunoassays, Ngo, Ed., Plenum Press, New York (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of catalytically active polypeptides of the present invention. The method comprises contacting a polypeptide of the present invention with a compound whose ability to bind to or modulate enzyme activity is to be determined. The polypeptide employed will have at least 20%, 30%, 40%, 50%, 60%, 70%, 80%, 90% or 95% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495-497 (1975).

Other suitable techniques involve selection of libraries of recombinant antibodies in phage or similar vectors (see, e.g., Huse et al., *Science* 246:1275-1281 (1989); and Ward et al., *Nature* 341:544-546 (1989); and Vaughan et al., *Nature Biotechnology* 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.* 14:845-851 (1996). Also, recombinant immunoglobulins may be produced. See, Cabilly, U.S. Pat. No. 4,816,567; and Queen et al., *Proc. Natl. Acad. Sci. U.S.A.* 86:10029-10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention may be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transformation of Cells

The method of transformation is not critical to the present invention; various methods of transformation are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein, can be used to construct an expression cassette which can be introduced into the desired plant. Isolated nucleic acid acids of the present invention can be introduced into plants according to techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421-477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in *Plant Cell, Tissue and Organ Culture, Fundamental Methods*, Eds. O. L. Gamborg and G. C. Phillips, Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobactetium tumefaciens* host will direct the insertion of the construct and adjacent marker into the plant cell DNA when the cell is infected by the bacteria. See, U.S. Pat. No. 5,591, 616.

The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci. U.S.A.* 82:5824 (1985). Ballistic transformation techniques are described in Klein et al., *Nature* 327:70-73 (1987).

*Agrobactedum tumefaciens*-meditated transformation techniques are well described in the scientific literature. See, for example Horsch et al., *Science* 233:496-498 (1984), and Fraley et al., *Proc. Natl. Acad. Sci.* 80:4803 (1983). For instance, *Agrobacterium* transformation of maize is described in U.S. Pat. No. 5,981,840. *Agrobacterium* transformation of soybean is described in U.S. Pat. No. 5,563,055.

Other methods of transformation include (1) *Agrobacterium rhizogenes*-mediated transformation (see, e.g., Lichtenstein and Fuller In: *Genetic Engineering*, Vol. 6, P. W. J. Rigby, Ed., London, Academic Press, 1987; and Lichtenstein, C. P. and Draper, J. In: *DNA Cloning*, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., *Plant Cell Physiol.* 25:1353 (1984)), and (3) the vortexing method (see, e.g., Kindle, *Proc. Natl. Acad. Sci. USA* 87:1228 (1990)).

DNA can also be introduced into plants by direct DNA transfer into pollen as described by Zhou et al., *Methods in Enzymology,* 101:433 (1983); D. Hess, *Intem Rev. Cytol.,* 107:367 (1987); Luo et al., *Plant Mol. Biol. Reporter,* 6:165 (1988). Expression of polypeptide coding polynucleotides can be obtained by injection of the DNA into reproductive organs of a plant as described by Pena et al., *Nature,* 325:274 (1987). DNA can also be injected directly into the cells of immature embryos and the rehydration of desiccated embryos as described by Neuhaus et al., *Theor. Appl. Genet.* 75:30 (1987); and Benbrook et al., in *Proceedings Bio Expo* 1986, Butterworth, Stoneham, Mass., pp. 27-54 (1986).

Animal and lower eukaryotic (e.g., yeast) host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell* 2:603-618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* can be achieved as described by Horsch et al., *Science*, 227:1229-1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467-486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Transgenic plants of the present invention can be homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated. Alternatively, propagation of heterozygous transgenic plants could be accomplished through apomixis.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: *Genome Mapping in Plants* (ed. Andrew H. Paterson) by Academic Press/R. G. Landis Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants which can be used in the method of the invention include monocotyledonous and dicotyledonous plants. Preferred plants include maize, wheat, rice, barley, oats, sorghum, millet, rye, soybean, sunflower, safflower, alfalfa, canola, cotton, or turf grass.

Seeds derived from plants regenerated from transformed plant cells, plant parts or plant tissues, or progeny derived from the regenerated transformed plants, may be used directly as feed or food, or further processing may occur.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

Other objects, features, advantages and aspects of the present invention will become apparent to those of skill from the following description. It should be understood, however, that the following description and the specific examples, while indicating certain embodiments of the invention, are given by way of illustration only. Various changes and modifications within the spirit and scope of the disclosed invention will become readily apparent to those skilled in the art from reading the following description and from reading the other parts of the present disclosure.

EXAMPLES

Example 1 cDNA Library Construction

A. Total RNA Isolation

Total RNA was isolated from maize tissues with TRIzol Reagent (Life Technology Inc. Gaithersburg, Md.) using a modification of the guanidine isothiocyanate/acid-phenol procedure described by Chomczynski and Sacchi (*Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

B. Poly(A)+ RNA Isolation

The selection of poly(A)+ RNA from total RNA was performed using PolyATract system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

C. cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between Not I and Sal I sites.

Example 2

Sequencing and cDNA Subtraction Procedures Used for Maize EST's

A. Sequencing Template Preparation

Individual colonies were picked and DNA was prepared either by PCR with M13 forward primers and M13 reverse primers, or by plasmid isolation. All the cDNA clones were sequenced using M13 reverse primers.

B. Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12-24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto individual agar plates with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40-50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in *Molecular Cloning: A Laboratory Manual, 2$^{nd}$* Edition). The following probes were used in colony hybridization:
1. First strand cDNA from the same tissue from which the library was made to remove the most redundant clones.
2. 48-192 most redundant cDNA clones from the same library based on previous sequencing data.
3. 192 most redundant cDNA clones in the entire corn sequence database.
4. A Sal-A20 oligonucleotide: TCG ACC CAC GCG TCC GAA AAA AAA AAA AAA AAA AAA, removes clones containing a poly A tail but no cDNA. See SEQ ID NO: 28.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

Example 3

Identification and Isolation of IPPK Genes Using PCR

The presence of the IPPK polynucleotide is analyzed by PCR using the commercially available Roche Expand High Fidelity PCR System. Template DNA was isolated using the CTAB method of Example 5C. The primers of SEQ ID NOS: 26 and 27 were used to amplify the gene of interest from various maize lines. The buffer and polymerase concentrations were used as defined for the kit with the DNA concentrations and cycling conditions as follows:

DNA Concentrations:
500 ng template DNA and 0.3 µM primers in a 50 µl PCR reaction mixture containing 200 µM dNTPs in buffer and polymerase provided by the Roche kit.

Thermocycling conditions are as follows (#cycles):
1 cycle:
  denature 2 min. at 94° C.
10 cycles:
  denature 15 sec. at 94° C.
  anneal 30 sec. at 55° C.
  elongate 60 sec. at 68° C.
15 cycles:
  denature 15 sec. at 94° C.
  anneal 30 sec at 55° C.
  elongate 60sec. +5 sec. each cycle at 68° C.
1 cycle:
  elongate 7 min. at 72° C.

The products of the PCR reaction were analyzed on agarose gels using standard molecular biology techniques.

Example 4

Vector Construction

All vectors were constructed using standard molecular biology techniques used by those of skill in the art (Sambrook et al., supra).

A. Vectors for Plant Transformation

Vectors were constructed for plant transformation using either particle bombardment or *Agrobacterium* transformation protocols. Plasmids were constructed by inserting IPPK expression cassettes, including the following: oleosin promoter::IPPK::nos terminator, oleosin promoter::ubiquiton intron::IPPK::nos terminator, or globulin 1 promoter::IPPK::globulin 1 terminator, into a descendent plasmid of pSB11 which contains the BAR expression cassette. Both the IPPK and the BAR expression cassettes were located between the right and left borders of the T-DNA.

For example, the *Zea mays* IPPK coding region, including the 5' UTR and 3' UTR was isolated from a full length EST clone as a 1.18 kb EcoRI/SapI fragment. The fragment was blunt ended using Klenow and the fragment inserted in frame into a EcoRV site of a plasmid between the oleosin promoter and the Nos terminator. Orientation was confirmed using a restriction enzyme digest. The oleosin promoter::IPPK::nos terminator transcription unit is flanked by BstEII sites which were used to excise the fragment and insert it into a binary vector containing the BAR selectable marker. The IPPK cassette is linked to the selectable marker between the right and left borders of the T-DNA. This vector was used for insert preparation for particle gun transformation as well as for generating *Agrobacterium* transformation vectors as described below. In this case, insert DNA for particle gun transformation was generated by isolating the 6.16 kb PmeI fragment from the vector.

The plasmid pSB11was obtained from Japan Tobacco Inc. (Tokyo, Japan). The construction of pSB11 from pSB21 and the construction of pSB21 from starting vectors is described by Komari et al. (1996, Plant J. 10:165-174). The T-DNA of the plasmid was integrated in to the superbinary plasmid pSB1 (Saito et al. EP 672 752 A1) by homologous recombination between the two plasmids. The plasmid pSB1 was also obtained from Japan Tobacco Inc. These plasmids were either used for particle bombardment transformation, or for *Agrobacterium*-mediated transformation after making a cointegrate in an appropriate *Agrobactenum* strain as described more fully below.

Competent cells of the *Agrobacterium* strain LBA4404 harboring pSB1 were created using the protocol as described by Lin (1995) in *Methods in Molecular Biology*, ed. Nickoloff, J. A. (Humana Press, Totowa, N.J.). The plasmid containing the expression cassettes was electroporated into competent cells of the *Agrobacterium* strain LBA4404 harboring pSB1 to create the cointegrate plasmid in *Agrobacterium*. Cells and DNA were prepared for electroporation by mixing 1 ul of plasmid DNA (~100 ng) with 20 ul of competent *Agrobacterium* cells in a 0.2 cm electrode gap cuvette (Bio-Rad Cat# 165-2086, Hercules, Calif.). Electroporation was performed in a Bio-Rad Micropulser (Cat# 165-2100, Hercules, Calif.) using the EC2 setting, which delivers 2.5kV to the cells. Successful recombination was verified by restriction analysis of the plasmid after transformation of the cointegrate plasmid back into *E. coli* DH5α cells.

B. Vectors for In Vitro Protein Expression in *E. Coli*

Vectors are constructed for protein expression of IPPKs (SEQ ID NOS: 1, 3, 5, 7, 9, 11, 13,15, 20, 22, and 24) in *E. coli* using standard protocols. Each IPPK sequence can be fused with GST to produce GST-tagged proteins which can facilitate purification.

If needed, cloning sites are introduced into the IPPK sequences by PCR. For example, a primer is designed which introduces a SmaI site to the 5' end of the sequence, and another primer is designed which introduces a NotI site to the 3' end of the sequence. Using these restriction sites, the IPPK sequence is cloned into the pGEX4T-2 vector (PHARMACIA BIOTECH) to generate the IPPK GST-tagged expression vector.

These expression vectors are used to transform *E. coli* strain DH5a using standard techniques. The expression of GST-tagged IPPK proteins and assay for substrate-specificity is further described in Example 7.

Example 5

Plant Transformation

A. Particle Bombardment Transformation and Regeneration of Maize Callus

Immature maize embryos from greenhouse or field grown High type II donor plants are bombarded with a plasmid containing an IPPK polynucleotide of the invention operably linked to an appropriate promoter. If the polynucleotide does not include a selectable marker, another plasmid containing a selectable marker gene can be co-precipitated on the particles used for bombardment. For example, a plasmid containing the PAT gene (Wohlleben et al. (1988) Gene 70:25-37) which confers resistance to the herbicide Bialaphos can be used. Transformation is performed as follows.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These are cultured on 560L agar medium 4 days prior to bombardment in the dark. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

A plasmid vector comprising a polynucleotide of the invention operably linked to the selected promoter is constructed. This plasmid DNA, plus plasmid DNA containing a PAT selectable marker if needed, is precipitated onto 1.1 μm (average diameter) tungsten pellets using a $CaCl_2$ precipitation procedure as follows: 100 μl prepared tungsten particles (0.6 mg) in water, 20 μl (2 μg) DNA in TrisEDTA buffer (1 μg total), 100 μl 2.5 M $CaCl_2$, 40 μl 0.1 M spermidine.

Each reagent is added sequentially to the tungsten particle suspension. The final mixture is sonicated briefly. After the precipitation period, the tubes are centrifuged briefly, liquid removed, washed with 500 ml 100% ethanol, and centrifuged again for 30 seconds. Again the liquid is removed, and 60 μl 100% ethanol is added to the final tungsten particle pellet. For particle gun bombardment, the tungsten/DNA particles are briefly sonicated and 5 μl spotted onto the center of each macrocarrier and allowed to dry about 2 minutes before bombardment.

The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Four to 12 hours post bombardment, the embryos are moved to 560P (a low osmoticum callus initiation medium similar to 560L but with lower silver nitrate), for 3-7 days, then transferred to 560R selection medium, an N6 based medium similar to 560P containing 3 mg/liter Bialaphos, and subcultured every 2 weeks. After approximately 10 weeks of selection, callus clones are sampled for PCR and activity of the polynucleotide of interest. Positive lines are transferred to 288J medium, an MS-based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the polynucleotide of interest.

B. *Agrobacterium*-Mediated Transformation and Regeneration of Maize Callus

For *Agrobacterium*-mediated transformation of maize, an IPPK nucleotide sequence of the present invention was introduced using the method of Zhao (U.S. Pat. No. 5,981,840, and PCT patent publication WO98/32326; the contents of which are hereby incorporated by reference).

Briefly, immature embryos were isolated from maize and the embryos contacted with a suspension of *Agrobacterium* containing a polynucleotide of the present invention, where the bacteria are capable of transferring the nucleotide sequence of interest to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step is contemplated. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

C. Transformation of Dicots with Transgene

An expression cassette, with a polynucleotide of the present invention operably linked to appropriate regulatory elements for expression can be introduced into embryogenic suspension cultures of soybean by particle bombardment using essentially the methods described in Parrott, W. A., L. M. Hoffman, D. F. Hildebrand, E. G. Williams, and G. B. Collins, (1989) Recovery of primary transformants of soybean, *Plant Cell Rep.* 7:615-617. This method, with modifications, is described below.

Seed is removed from pods when the cotyledons are between 3 and 5 mm in length. The seeds are sterilized in a bleach solution (0.5%) for 15 minutes after which time the seeds are rinsed with sterile distilled water. The immature cotyledons are excised by first cutting away the portion of the seed that contains the embryo axis. The cotyledons are then removed from the seed coat by gently pushing the distal end of the seed with the blunt end of the scalpel blade. The cotyledons are then placed (flat side up) SB1 initiation medium (MS salts, B5 vitamins, 20 mg/L 2,4-D, 31.5 g/l sucrose, 8 g/L TC Agar, pH 5.8). The Petri plates are incubated in the light (16 hr day; 75-80 µE) at 26° C. After 4 weeks of incubation the cotyledons are transferred to fresh SB1 medium. After an additional two weeks, globular stage somatic embryos that exhibit proliferative areas are excised and transferred to FN Lite liquid medium (Samoylov, V. M., D. M. Tucker, and W. A. Parrott (1998) Soybean [*Glycine max* (L.) Merrill] embryogenic cultures: the role of sucrose and total nitrogen content on proliferation. *In Vitro Cell Dev. Biol.-Plant* 34:8-13). About 10 to 12 small clusters of somatic embryos are placed in 250 ml flasks containing 35 ml of SB172 medium. The soybean embryogenic suspension cultures are maintained in 35 mL liquid media on a rotary shaker, 150 rpm, at 26° C. with florescent lights (20 µE) on a 16:8 hour day/night schedule. Cultures are sub-cultured every two weeks by inoculating approximately 35 mg of tissue into 35 mL of liquid medium.

Soybean embryogenic suspension cultures are then transformed using particle gun bombardment (Klein et al. (1987) *Nature* (London) 327:70, U.S. Pat. No. 4,945,050). A BioRad Biolistic™ PDS1000/HE instrument can be used for these transformations. A selectable marker gene, which is used to facilitate soybean transformation, is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is agitated for three minutes, spun in a microfuge for 10 seconds and the supernatant removed. The DNA-coated particles are washed once in 400 µL 70% ethanol and resuspended in 40 µL of anhydrous ethanol. The DNA/particle suspension is sonicated three times for one second each. Five µL of the DNA-coated gold particles are then loaded on each macro carrier disk.

Approximately 300-400 mg of a two-week-old suspension culture is placed in an empty 60×15 mm Petri dish and the residual liquid removed from the tissue with a pipette. Membrane rupture pressure is set at 1100 psi and the chamber is evacuated to a vacuum of 28 inches mercury. The tissue is placed approximately 8 cm away from the retaining screen, and is bombarded three times. Following bombardment, the tissue is divided in half and placed back into 35 ml of FN Lite medium.

Five to seven days after bombardment, the liquid medium is exchanged with fresh medium. Eleven days post bombardment the medium is exchanged with fresh medium containing 50 mg/mL hygromycin. This selective medium is refreshed weekly. Seven to eight weeks post bombardment, green, transformed tissue will be observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos, or tissue is regenerated into whole plants by maturation and germination of individual embryos.

D. DNA Isolation from Callus and Leaf Tissues

In order to screen putative transformation events for the presence of the transgene, genomic DNA is extracted from calluses or leaves using a modification of the CTAB (cetyltriethylammonium bromide, Sigma H5882) method described by Stacey and Isaac (1994). Approximately 100-200 mg of frozen tissues is ground into powder in liquid nitrogen and homogenised in 1 ml of CTAB extraction buffer (2% CTAB, 0.02 M EDTA, 0.1 M Tris-Cl pH 8, 1.4 M NaCl, 25 mM DTT) for 30 min at 65° C. Homogenised samples are allowed to cool at room temperature for 15 min before a single protein extraction with approximately 1 ml 24:1 v/v chloroform:octanol is done. Samples are centrifuged for 7 min at 13,000 rpm and the upper layer of supernatant collected using wide-mouthed pipette tips. DNA is precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five µl RNAse A is added to the samples and incubated at 37° C. for 1 h.

For quantification of genomic DNA, gel electrophoresis is performed using a 0.8% agarose gel in 1×TBE buffer. One microliter of the samples are fractionated alongside 200, 400, 600 and 800 ng µl$^{-1}$ λ uncut DNA markers.

Example 6

Identification of High Phosphorus/Low Phytate Transgenic Corn Lines

The resulting transformants are screened for inorganic phosphorus and/or phytate levels using the colorimetric assays as described below. The extraction procedure used is compatible with both assays. The calorimetric assays can be performed sequentially or simultaneously. Putative events are usually initially screened for increased levels of inorganic phosphorous compared to wild type control and then further characterized by the phytate assay.

A. Sample Preparation

Individual kernels are crushed to a fine powder using a ball mill grinding device. Grinding of certain samples, for example high oil corn lines, can be facilitated by chilling the sample in the grinding apparatus at −80° C. for 2 hours prior to grinding. Transfer 25-35 mg of each ground sample to new 1.5 ml microfuge tube. Extract each sample with 1 ml of 0.4N hydrochloric acid (HCl) for 3.5 hours at room temperature with shaking to keep the meal suspended. Transfer 1 ml of this suspension to a 1.1 ml Megatiter tube (Cat# 2610, Continental Labs) and place into the 96-well Megatiter plate (Cat# 2405, Continental Labs). Clarify the extract by low-speed centrifugation, for example 4000 rpm for 15 minutes in a Jouan centrifuge. The clarified supernatant is used for the assays described in sections 6B and 6C below.

B. Quantitative Inorganic Phosphate Assay

This assay is performed in duplicate for each sample. For each sample mix a 200 ul aliquot of clarified extract with 100 µl 30% trichloroacetic acid (TCA). Clarify by low speed centrifugation. Transfer 50 µl clarified supernatant to a 96-well microtiter plate. Add 100 µl of the color reagent (7 parts 0.42% ammonium molybdate in 1N H2SO4:1 part 10% ascorbic acid) and incubate at 37° C. for 30 minutes. A phosphate standard curve is generated using $NaH_2PO_4$ in the range of 0-160 nmol diluted from a 10 mM stock solution in 2 parts 0.4N HCl:1 part 30% TCA. Measure the absorbance at 800 nm.

C. Quantitative Phytate Assay

This assay is modified from Haug and Lantzsch (1983) J. Sci. Food Agric. 34:1423-1426. This assay is performed in duplicate for each sample. Phytate standard (Cat# P-7660, Sigma Chemical Co., St. Louis, Mo.) stock solution is made by dissolving 150 mg phytate in 100 ml distilled water (DDW). Standards in the range of 0-35 µg/ml are made by dilution with 0.2N HCl. Samples are prepared in 96-well microtiter plates by mixing 35 µl of clarified supernatant (from 6A) with 35 µl of DDW, add 140 µl ferric solution (0.2 g ammonium iron (III) sulphate dodecahydrate (Merck Art 3776)/liter in 0.2N HCl). Plates are sealed and incubated for 30 minutes at 99° C., then cooled to 4° C. Plates are kept in an ice-water bath for 15 minutes then transferred to room temperature for 20 minutes. Centrifuge the plates at low speed to pellet precipitate, for example spin 30 minutes at 4000 rpm in a Jouan centrifuge. After centrifugation transfer 80 µl clarified supernatant to a new 96-well plate and mix with 120 ul 2,2'-bipyridine solution (10 g 2,2'-bipyridine (Merck Art. 3098), 10 ml thioglycolic acid (Merck Art. 700) in DDW to 1 liter).

Each plant identified as a potential high phosphorus transgenic is tested again to confirm the original elevated phosphorus reading. Confirmed high phosphorous lines are selected on the basis of uniformity for the trait. Transformants which are positive with the calorimetric assays will then be subjected to more rigorous analyses to include Southern, Northern and Western blotting and/or quantitation and identification of phytic acid and inositol phosphate intermediates by HPLC.

Example 7

Determining the Substrate Specificity of the IPPK Clones

A. Expression of IPPK and Purification

A single colony of *E. coli* strain DH5α containing a GST-tagged IPPK expression vector described in Example 4 is cultured overnight at 37° C. in LB medium containing ampicillin (Amp). The overnight culture is diluted 1:10 with fresh LB+Amp and incubated at 37° C. with vigorous agitation until the A600 reading of the culture is in the range of 1-2 O.D. units. GST fusion protein expression is induced by the addition of IPTG to the culture to a final concentration of 1 µM. The cultures are incubated at 37° C. with agitation for an additional 3 hrs.

Cells are harvested by centrifugation at 7,700×g for 10 minutes at 4° C. The cells are lysed on ice by sonication and the lystate is clarified by centrifugation at 12,000×g for 10 minutes at 4° C. The GST-IPPK proteins are affinity purified by batch absorption to Glutathione Sepharose 4B bead resin (Bulk GST Purification kit, Pharmacia Biotech) at a ratio of 1 ml bed volume of the 50% Glutathione Sepharose 4B slurry per 100 ml clarified lysate. Following the conditions detailed in the manufacturer's instructions, the beads are washed and GST-tagged IPPK protein eluted with 10 mM reduced glutathione in 50 mM Tris-HCl (pH 8.0). After elution, glycerol is added to a final concentration of 50% and purified GST-IPPK proteins are stored in 50% glycerol at −20° C. The protein concentration is adjusted to approximately 50 µg/µl.

B. Assay for IPPK Activity and Substrate Specificity

Purified GST-IPPK fusion proteins are used in an inositol polyphosphate kinase activity assay. The activity assay is performed in a volume of 25 µl. The assay mixture contains 20 mM HEPES, pH 7.2, 6 mM $MgCl_2$, 10 mM LiCl, 1 mM DTT, 40 µM inositol phosphate substrate, 40 µM ATP, 0.5 µl γ-$^{32}$P-ATP (3000 Ci/mmol) and 5 µl enzyme per reaction. The reaction mixture is incubated at 30° C., or room temperature, for 30 minutes. The reaction is stopped by the addition of 2.8 µl stopping solution (3M HCl, 2M $KH_2PO_4$) to the 25 µl reaction. One microliter samples of each reaction, along with inositol phosphate standards, are separated on a polyethyleneimine (PEI)-cellulose thin layer chromatography plate (Merck) with 0.5M HCl according to Spencer et al. (In *Methods in Inositide Research*, (1990) pp. 39-43, Ed. R. F. Irvine, Raven Press, New York). After separation, the TLC plate was air-dried at 70° C., wrapped in plastic wrap and exposed to X-ray film to detect the $^{32}$P-labelled reaction products. The reaction products were quantified by cutting the spot out of the TLC plate and measuring the radioactivity in a liquid scintillation counter. The identity of the reaction product was confirmed by comparing the distance migrated to the migration of the inositol phosphate standard controls run on each TLC plate. Several inositol phosphate substrates are tested to determine the substrate specificity of the IPPK enzymes. The other substrates tested under the same conditions above are: Ins(1)P, Ins(2)P, Ins(4)P, Ins(1,4)$P_2$, Ins(4,5)$P_2$, Ins(1,3,4)$P_3$, Ins(3,4,5)$P_3$, Ins(1,4,5)$P_3$, Ins(3,4,5,6)$P_4$, Ins(1,3,4,6)$P_4$, Ins(1,3,5,6)$P_4$, and Ins(1,3,4,5,6)$P_5$.

Example 8

ITPK Corn Knockout Mutants

Mu-tagged corn populations (TUSC) are screened for knockouts of the IPPK gene, using the primers specific to the IPPK sequence of interest paired with a Mu-primer in PCR reactions. Lines identified as having a Mu-insertion in the IPPK gene are screened by further assays. Kernels from these lines are screened for phytate and inorganic phosphate levels versus phytate mutants Lpa1 and Lpa2, as well as wild type controls, using the assays described in Example 6.

Example 9

Myo-inositol Assay

Putative events can also be screened to determine the effect the transgene may have on myo-inositol levels in the kernel using a gas chromatography/mass spectrometry method.

Briefly, 20 representative whole, mature, dry kernels are ground to a fine meal in a ball mill apparatus. Each sample is analyzed in triplicate. For extraction, three aliquots of 0.5 g meal for each sample is extracted with 5 ml of 50% v/v ethyl alcohol (1:1 100% ethyl alcohol:DDW) at room temperature for one hour with vigorous shaking. The extract supernatant is decanted and filtered through a 0.45 µm syringe filter. The meal residue is re-extracted with 5 ml of fresh 50% ethanol following the same procedure, combining the two filtrates. Each sample is vortexed, and a 1 ml aliquot taken and evaporated to dryness in a SpeedVac at medium heat.

A myo-inositol standard stock of 10 mg/ml is made in double distilled water (DDW) which is used to make a 1 mg/ml standard solution working stock. Aliquots of 50 µl, 100 µl, 200 µl and 300 µl are transferred to new tubes and evaporated to dryness in a SpeedVac as described above. This calibration set covers a concentration range of 5 µg/ml to 30 µg/ml of each component.

Thoroughly dried standards and samples are resuspended in 50 µl pyridine. To this, 50 µl of 100:1 trimethylsilylimadazole-trimethylchlorosilane (TMSI-TMCS) is added to each sample. Samples are compromised if a precipitate forms. Tubes are sealed, vortexed and incubated 15 min. at 60° C. After incubation, 1 ml of 2,2,4-trimethylpentane and 0.5 ml DDW are added. Vortex samples and centrifuge at low speed (2000 rpm) for 5 minutes. The top, organic layer is transferred to a 2 ml autosampler vial which can be stored at 4° C. until it can be analyzed.

Samples are analyzed on a Hewlett-Packard 5890/7673/5972 Gas Chromatography/Mass Spectrometry (GC/MS) apparatus using a Hewlett-Packard 30 m×0.25 mm i.d.×0.25 µm film thickness 5MS column under the following conditions:

Inlet temperature: 250° C.
Injection Volume: 1 ml
Split Ratio: Splitless
Oven Temperature: 70° C. initial, hold for 2 min.
Ramp at 25/min. to 170° C., hold for 0 min.
Ramp at 5/min. to 215° C., hold for 0 min.
Hold for 5 min., for a 23.4 min. total run time
Detector Temperature: 250° C.
Carrier Gas: Helium, 36.6 cm/sec at 70° (1 ml/min.)
Full scan (m/z 50-650), 5 min. data collection delay. Results are reported as µg/ml for the final sample analyzed by the GC/MS, this concentration is multiplied by a factor of 20 before using to calculate µg/g dry weight tissue. The moisture content of the mature kernels is determined from a separate aliquot of each experimental sample so that the results can be adjusted to a dry weight basis.

Myo-inositol levels are quantified as follows:

$$\frac{\mu g\ myo\text{-}inositol}{g\ dry\ wt.\text{tissue}} = \frac{\mu g(X20)}{ml\ sample} \times \frac{1ml\ sample}{1ml\ extract} \times \frac{10ml\ extract}{0.5g\ tissue}$$

Example 10

HPLC of Phytate and Inositol Phosphate Intermediates

Phosphorous and inositol phosphate intermediates associated with phytic acid in wheat, corn, and soybean seeds can be identified and quantitated using gradient anion-exchange chromatography HPLC with conductivity detection. Phytate and the intermediate inositol phosphates can be identified using this method. However, the method practiced currently has been optimized for phytate, it is not optimized for quantitation of intermediate inositol phosphates. For other HPLC separations of inositol phosphates see also Anonymous, (1990) "Analysis of inositol phosphates" *Dionex Corp. Application Note AN* 65; Xu, P., Price, J., and Aggett, P. (1992) *Progress in Food and Nutrition Science* 16:245262; Rounds, M. A. and Nielsen, S. S. (1993) *J. Chromatogr* 653:148-152; and Trugo, L. and von Baer, D. (1998) *Association for animal*

*production*, publication 93:1128. Inositol phosphates can also be identified by thin-layer chromatographic methods, see for example Spencer, C. E. L et al. (1990) Ch. 4 in *Methods in Inositide Research*, Ed. R. F. Irving, Raven Press, Ltd., New York pp. 39-43; and Hatzack, F. and Rasmussen, S. K. (1999) *J. Chromatogr B* 736:221-229.

For anion-exchange HPLC, a phytic acid standard range of 0.25, 0.5, 1.0, 2.0 and 3.0 mg/ml is prepared in 0.4 M hydrochloric acid (HCl) from a 20 mg/ml working stock in 0.4 M HCl. Seed samples are prepared by grinding seeds to a fine meal in a ball mill grinding apparatus. Replicate aliquots are weighed and extracted in 0.4M HCl in a ratio of 0.1 g meal/1 ml 0.4M HCl. Usually 5 ml 0.4M HCl is used to extract 0.5 g corn or wheat meal while 15 ml 0.4M HCl is used to extract 1.5 g soy meal. After the addition of the extraction buffer, the samples are extracted with moderate-vigorous shaking for 2 hrs. at room temperature, then transferred to 4° C. overnight without shaking. The supernatants from corn and wheat are clarified by low-speed centrifugation. Due to the high fat content, the low-speed supernatant from soy sample extracts is further clarified by ultracentrifugation at 55,000 rpm at 4° C. for 1 hour. After ultracentrifugation, the clear, middle layer is removed with a needle or extended tip disposable transfer pipette. Clarified samples are filtered through a 0.45 µm syringe filter and stored at 4° C. until analysis. Just before analysis, an aliquot of each sample is filtered with a Millipore Durapore ULTRAFREE-MC 0.22 µm centrifugal filter unit, or equivalent.

Samples are subjected to anion-exchange HPLC separation by a linear gradient of 0.06-0.118M sodium hydroxide (NaOH) in 1% isopropyl alcohol on a Dionex OmniPac PAX-100 column at a flow rate of 1 ml/min. The total run time is 30 min. with data collection from 0 to 20 minutes. Signal collection is set at 0.5 Hz, detector units in µS, current at 300 mA, with the Detection Stablilizer regulated at 30° C. and temperature compensation at 1.7.

Twenty-five microliters extract is loaded onto the column. Soybean samples appear to cause column performance deterioration, therefore it is helpful to interject short column cleaning run between samples. The cleaning run comprises a series of injections for 1M HCl, 1M NaOH, and 90% acetonitrile.

Example 11

Suppressing IPPK in Transgenic Maize Seeds Reduces Phytic Acid and Increases Pi (Inorganic Phosphorus)

Two expression inhibiting constructs were made using the ZM IPPK polynucleotide of SEQ ID NO:1. The constructs were transformed into maize using the protocol described in Example 5.

PHP 17562:

PHP17562 (SEQ ID NO: 39) comprised the Ubiquitin intron inserted between the Oleosin (Ole) promoter and ZM IPPK polynucleotide of SEQ ID NO:1.

Transgenic T1 seeds confirmed by PCR to be transgenic, were screened for elevated inorganic phosphate (Pi) content and phytic acid level using the assay described in Example 6. Seeds with inhibited expression of IPPK also showed phytic acid reduction and increased Pi.

A segregating ear of PHP17562 with ten T1 seeds confirmed by PCR to contain inhibited expression of IPPK was analyzed for phytic acid reduction and increased Pi. A clear association was seen between reduced IPPK gene expression and decreased phytic acid and increased Pi.

PHP 17571:

PHP17571 (SEQ ID NO: 38) comprised the Globulin 1 (Glb1) promoter in 3' to 5' orientation, the complementary strand of SEQ ID NO:1 and the Glb1 terminator in 5' to 3' orientation.

Transgenic T1 seeds confirmed by PCR to be transgenic, were screened for elevated inorganic phosphate (Pi) content and phytic acid level using the assay described in Example 6. Seeds with inhibited expression of IPPK also showed phytic acid reduction and increased Pi.

HPLC also was used to quantify phytate and inositol phosphate intermediates as described in Example 10. IPPK-inhibited kernels accumulated inositol phosphate (InsP) and intermediates (InsP$_{4/3}$) as shown in the following table:

TABLE 1

| Phenotype | (umol/g) | | |
|---|---|---|---|
| | Phytate | InsP | InsP$_{4/3}$ |
| Wild-type | 11.51 | 0.14 | nd |
| Inhibited IPPK | 5.75 | 2.20 | 1.90 |

(*nd = not detectable)

The reduction of transgenic IPPK was shown to be inheritable: T2 seed from maize transformed with construct 17571 were analyzed for presence of IPPK expression, phytic acid level and Pi content. Ten kernels were chosen from a segregating ear: eight kernels having suppressed levels of IPPK and two wild-type kernels. The low phytic acid-high Pi phenotype was clearly present in the transgenic kernels.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated nucleic acid comprising a member selected from the group consisting of:
   (a) a polynucleotide which encodes the polypeptide of SEQ ID NO: 2;
   (b) a polynucleotide having the sequence set forth in SEQ ID NO: 1; and
   (c) a polynucleotide complementary to the full length of the polynucleotide of (a) or (b).

2. An expression cassette comprising at least one nucleic acid of claim 1 operably linked to a promoter.

3. A non-human host cell containing at least one expression cassette of claim 2.

4. A transgenic plant comprising at least one expression cassette of claim 2.

5. A seed from the transgenic plant of claim 4 wherein the seed comprises the expression cassette.

6. A method for modulating inositol polyphosphate kinase (IPPK) activity or levels in a plant, comprising:
   (a) transforming a plant cell with at least one expression cassette of claim 2; and
   (b) growing the transformed host cell under conditions sufficient to modulate IPPK activity in the plant.

7. A plant produced by the method of claim 6.

8. The transgenic plant of claim 7, wherein the plant is corn.

9. The plant of the method of claim 6 wherein the level of phytate in the plant is reduced.

10. The plant of the method of claim 6 wherein the level of non-phytate phosphorous in the plant is increased.

* * * * *